United States Patent

Wenger et al.

[11] Patent Number: 4,812,164
[45] Date of Patent: Mar. 14, 1989

[54] HERBICIDAL HETEROCYCLIC COMPOUNDS

[75] Inventors: Jean Wenger, Uster; Paul Winternitz, Greifensee, both of Switzerland

[73] Assignee: Hoffmann-La Roche Inc., Nutley, N.J.

[21] Appl. No.: 96,432

[22] Filed: Sep. 15, 1987

[30] Foreign Application Priority Data

Sep. 18, 1986 [CH] Switzerland ............... 3741/86
Jul. 24, 1987 [CH] Switzerland ............... 2828/87

[51] Int. Cl.$^4$ ................. A01N 43/54; C07D 239/54
[52] U.S. Cl. ........................... 71/92; 544/253; 544/285; 544/309; 544/312; 544/313
[58] Field of Search ............ 544/253, 285, 309, 311, 544/312, 313; 71/92

[56] References Cited

U.S. PATENT DOCUMENTS

| | | | |
|---|---|---|---|
| 3,452,017 | 6/1969 | Petersen | 544/309 |
| 3,497,515 | 2/1970 | Loux | 544/309 |
| 3,580,913 | 5/1971 | Lutz | 544/309 |
| 3,838,128 | 9/1974 | Lutz | 544/309 |
| 3,869,457 | 3/1975 | Lutz | 544/309 |
| 3,920,653 | 11/1975 | Wenzelburger et al. | 544/253 |
| 4,266,056 | 5/1981 | Henrick et al. | 544/311 |

FOREIGN PATENT DOCUMENTS

| | | | |
|---|---|---|---|
| 57280 | 8/1982 | European Pat. Off. | 544/311 |
| 968661 | 9/1964 | United Kingdom | 544/309 |

*Primary Examiner*—Nicholas S. Rizzo
*Assistant Examiner*—Cecilia Shen
*Attorney, Agent, or Firm*—Jon S. Saxe; George M. Gould; Dennis P. Tramaloni

[57] ABSTRACT

The invention is concerned with novel $C_{1-4}$-alkyl, $C_{2-4}$-alkenyl and $C_{3\,or\,4}$-alkynyl enol ethers of 3-aryluracils of the formula

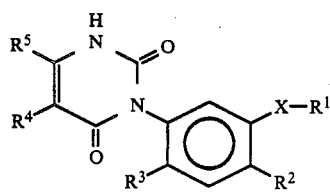

I' wherein $R^1$, $R^2$, $R^3$, $R^4$, $R^5$ and X are as defined in the specification, their manufacture, weed control compositions which contain such enol ethers as the active substance and the use of the active substances or compositions for the control of weeds. The invention is also concerned with certain novel intermediates, some of which possess herbicidal activity, and with weed control compositions containing such active substances.

15 Claims, No Drawings

HERBICIDAL HETEROCYCLIC COMPOUNDS

DETAILED DESCRIPTION OF THE INVENTION

The present invention is concerned with heterocyclic compounds, namely $C_{1-4}$-alkyl, $C_{2-4}$-alkenyl and $C_3$ or 4-alkynyl enol ethers of 3-aryluracils of the general formula

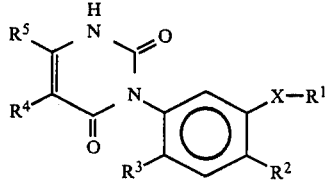     I' wherein
$R^1$ signifies $C_{1-8}$-alkyl, $C_{2-6}$-alkenyl, $C_{2-6}$-alkynyl, $C_{2-8}$-alkoxyalkyl or a group
$R^2$ signifies halogen or cyano,
$R^3$ signifies hydrogen or halogen.
$R^4$ signifies hydrogen, fluorine or $C_{1-4}$-alkyl.
$R^5$ signifies $C_{1-4}$-alkyl or $C_{1-4}$-haloalkyl.
$R^4$ and $R^5$ together signify tri- or tetramethylene,
$R^6$ and $R^7$ each independently signify $C_{1-4}$-alkyl,
m signifies 1 or 2 and
X signifies O, O-C(O), O-C(O)-O or C(O)-O.

The enol ethers in accordance with the invention thus embrace the compounds of the formulae

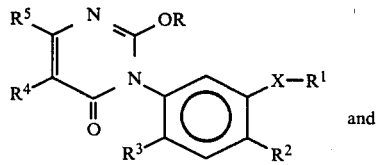     Ia and

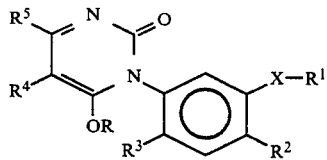     Ib wherein $R^1$-$R^5$ and X have the significances given above and R signifies $C_{1-4}$-alkyl, $C_{2-4}$-alkenyl or $C_3$ or 4-alkynyl.

The enol ethers in accordance with the invention have herbicidal activity and are suitable as active substances of weed control compositions. Accordingly, the invention also embraces weed control compositions which contain enol ethers in accordance with the invention as active substances, a process for the manufacture of these compounds as well as the use of such enol ethers or compositions for the control of weeds.

In the above definitions of the residues $R^2$, $R^3$ and $R^5$ "halogen" per se or "halo" as part of the haloalkyl group embraces fluorine, chlorine, bromine and iodine. The haloalkyl group ($R^5$) can have one or more similar or different halogen atoms, trifluoromethyl being an example of a multiply halogenated alkyl residue. The alkyl, alkenyl and alkynyl residues (R, $R^1$, $R^4$, $R^5$, $R^6$, $R^7$) can be straight-chain or branched, and this also applies to the or each alkyl part of the alkoxyalkyl and haloalkyl groups ($R^1$, $R^5$).

A sub-group of enol ethers in accordance with the invention comprises the $C_{1-4}$-alkyl, $C_3$ or 4-alkenyl and $C_3$ or 4-alkynyl enol ethers of those 3-aryluracils of formula I' in which $R^1$ signifies $C_{1-6}$-alkyl, $C_{3-6}$-alkenyl, $C_{3-6}$-alkynyl, $C_{2-7}$-alkoxyalkyl or a group $$-(CH_2)_m-O-N=C\begin{matrix}R^6\\R^7\end{matrix}$$

and $R^2$ signifies halogen, and $R^3$, $R^4$, $R^5$, $R^6$, $R^7$, m and X have the significances given above.

Independently of one another $R^2$ preferably signifies chlorine or bromine, $R^3$ preferably signifies fluorine and $R^5$ preferably signifies $C_{1-4}$-fluoroalkyl, especially trifluoromethyl or pentafluoroethyl.

Especially preferred individual compounds in accordance with the invention are:
Isopropyl 2-chloro-4-fluoro-5-[2-methoxy-6-oxo-4-pentafluoroethyl-1(6H)-pyrimidinyl]-benzoate,
isopropyl 2-chloro-4-fluoro-5-[5-fluoro-2-methoxy-6-oxo-4-pentafluoroethyl-1(6H)-pyrimidinyl]-benzoate,
1-(4-chloro-2-fluoro-5-isopropoxyphenyl)-2-methoxy-4-trifluoromethyl-6(1H)-pyrimidinone,
1-(4-chloro-2-fluoro-5-isopropoxyphenyl)-2-methoxy-4-pentafluoroethyl-6(1H)-pyrimidinone,
1-(4-chloro-2-fluoro-5-isopropoxyphenyl)-5-fluoro-2-methoxy-4-pentafluoroethyl-6(1H)-pyrimidinone,
isopropyl 2-chloro-4-fluoro-5-[2-methoxy-6-oxo-4-trifluoromethyl-1(6H)-pyrimidinyl]-benzoate,
isopropyl 2-chloro-4-fluoro-5-[5-fluoro-2-methoxy-6-oxo-4-trifluoromethyl-1(6H)-pyrimidinyl]-benzoate,
1-(4-chloro-2-fluoro-5-propargyloxyphenyl)-2-methoxy-4-trifluoromethyl-6(1H)-pyrimidinone,
methyl 2-chloro-4-fluoro-5-[2-methoxy-6-oxo-4-pentafluoroethyl-1(6H)-pyrimidinyl]-benzoate,
ethyl 2-chloro-4-fluoro-5-[2-methoxy-6-oxo-4-pentafluoroethyl-1(6H)-pyrimidinyl]-benzoate,
n-propyl 2-chloro-4-fluoro-5-[2-methoxy-6-oxo-4-pentafluoroethyl-1(6H)-pyrimidinyl]-benzoate,
n-butyl 2-chloro-4-fluoro-5-[2-methoxy-6-oxo-4-pentafluoroethyl-1(6H)-pyrimidinyl]-benzoate and
2-methoxyethyl 2-chloro-4-fluoro-5-[2-methoxy-6-oxo-4-pentafluoroethyl-1(6H)-pyrimidinyl]-benzoate.

Other representative compounds in accordance with the invention are those of the formulae

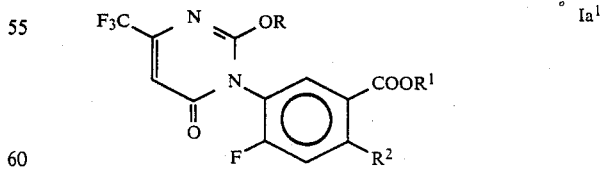     Ia¹

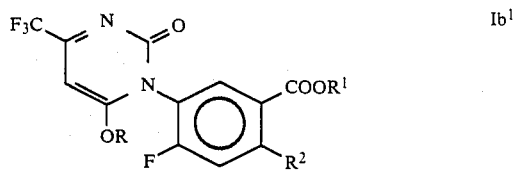     Ib¹

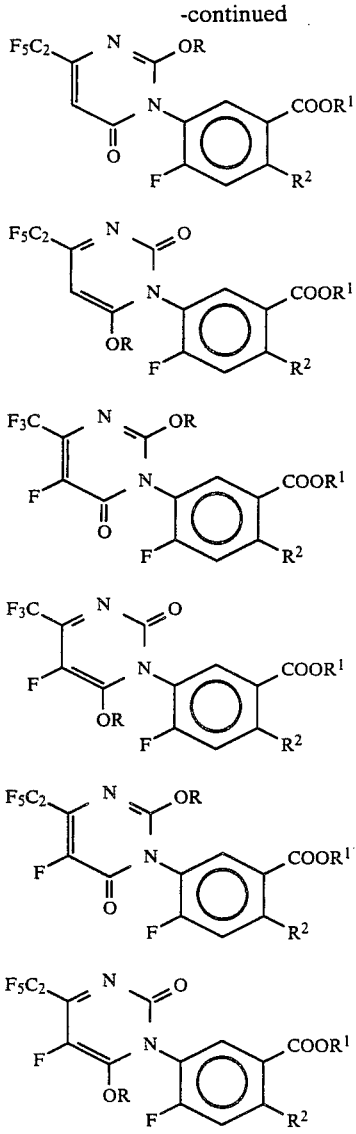

in which R, R[1] and R[2] have the significances given in Table 1 hereinafter:

TABLE 1

| R | R[1] | R[2] |
|---|---|---|
| CH₃ | CH₃ | Cl |
| " | " | Br |
| " | C₂H₅ | Cl |
| " | " | Br |
| " | nC₃H₇ | Cl |
| " | " | Br |
| " | isoC₃H₇ | Cl |
| " | " | Br |
| " | nC₄H₉ | Cl |
| " | " | Br |
| " | —CH₂OCH₃ | Cl |
| " | " | Br |
| " | —CH₂CH=CH₂ | Cl |
| " | " | Br |
| " | —CH₂C≡CH | Cl |
| " | " | Br |
| C₂H₅ | CH₃ | Cl |
| " | " | Br |
| " | C₂H₅ | Cl |
| " | " | Br |
| " | isoC₃H₇ | Cl |
| " | " | Br |

TABLE 1-continued

| R | R[1] | R[2] |
|---|---|---|
| isoC₃H₇ | isoC₃H₇ | Cl |
| " | " | Br |
| —CH₂CH=CH₂ | " | Cl |
| " | " | Br |
| —CH₂C≡CH | " | Cl |
| " | " | Br | as well as those of the formulae

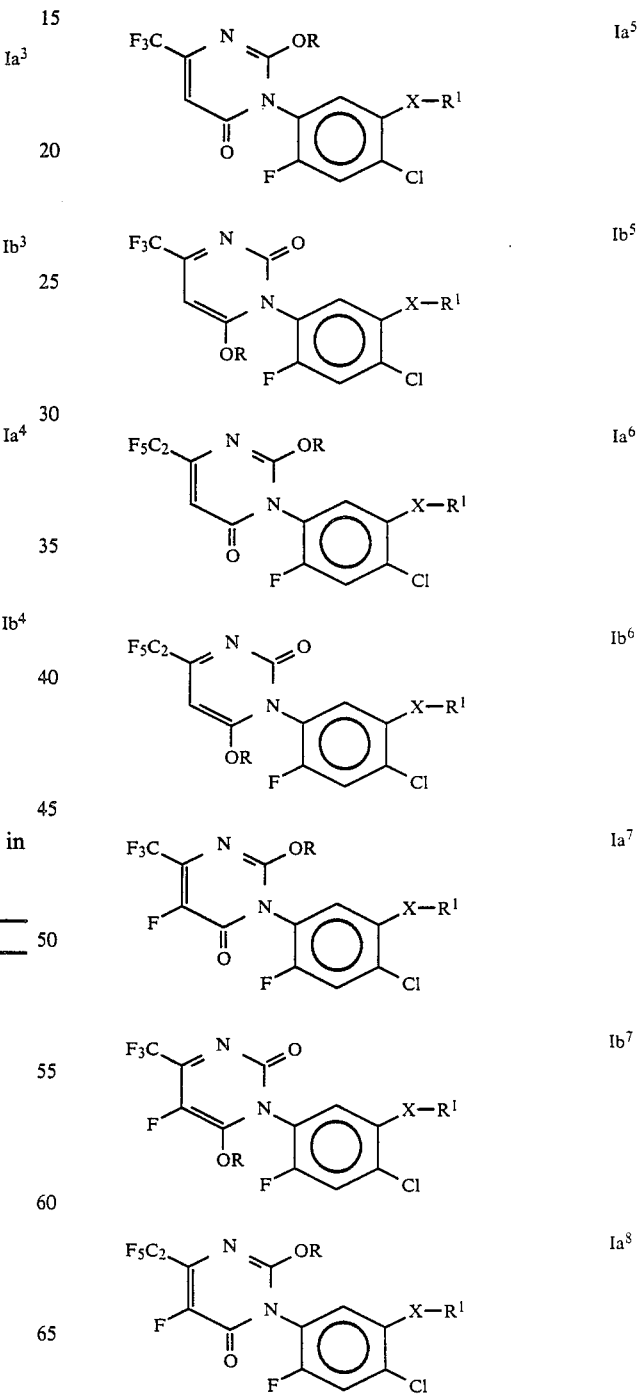

-continued

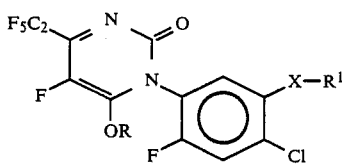
Ib[8]

wherein R, R[1] and X have the significances given in Table 2 hereinafter:

TABLE 2

| R | R[1] | X |
|---|---|---|
| CH$_3$ | CH$_3$ | O |
| " | isoC$_3$H$_7$ | " |
| " | —CH$_2$CH=CH$_2$ | " |
| " | —CH$_2$C≡CH | " |
| " | —CH$_2$OCH$_3$ | " |
| " | CH$_3$ | O—C(O) |
| " | " | O—C(O)—O |
| C$_2$H$_5$ | " | O |
| " | isoC$_3$H$_7$ | " |
| " | —CH$_2$C≡CH | " |
| isoC$_3$H$_7$ | isoC$_3$H$_7$ | " |
| " | —CH$_2$C≡CH | " |
| C$_2$H$_5$ | CH$_3$ | O—C(O) |
| " | " | O—C(O)—O |

The process in accordance with the invention for the manufacture of the enol ethers comprises (a) treating a uracil derivative of the general formula

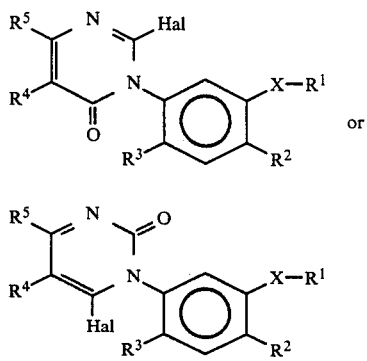

IIa or

IIb wherein R[1]; –R[5] and X have the significances given above and Hal signifies chlorine or bromine, with an alcohol ROH in the presence of an organic base or with the corresponding metal alcoholate of the general formula

RO⊖M⊕    III wherein R signifies C$_{1-4}$-alkyl, C$_{2-4}$-alkenyl or C$_3$ or 4-alkynyl and M⊕ signifies an equivalent of a metal ion.

(b) subjecting a 3-aryluracil of general formula I' given above in which X signifies O or C(O)-O to an appropriate alkylation under basic reaction conditions, or (c) replacing the hydroxy group in a uracil derivative of the general formula

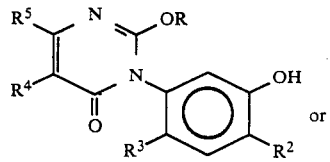
IVa or

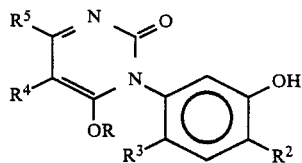
IVb wherein R, R[2], R[3], R[4] and R[5] have the significances given above, in a manner known per se by the substituent X'-R[1] in which X' stands for O, O-C(O) or O-C(O)-O, or (d) appropriately esterifying a benzoic acid of the general formula

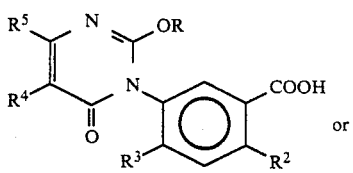
Va or

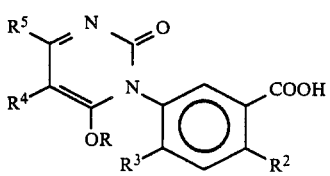
Vb wherein R, R[2], R[3], R[4] and R[5] have the significances given above, or a reactive derivative thereof, and isolating the desired enol ether.

In process variant a) the term "metal ion" stands, in particular, for an alkali metal ion, e.g. the sodium or potassium ion, or an alkaline earth metal ion, e.g. the calcium or magnesium ion. The sodium ion is the preferred metal ion. When the alcohol ROH is used, the base is especially an organic tertiary base such as triethylamine or pyridine.

The reaction is conveniently effected in an excess of the corresponding alcohol ROH as the diluent and at temperatures between 0° C. and 50° C., preferably at room temperature.

After working-up the reaction mixture the thus-obtained compound in accordance with the invention can be isolated and purified according to methods known per se, e.g. column chromatography and/or crystallization.

This process variant is especially suitable for the manufacture of those compounds Ia and Ib in accordance with the invention in which X signifies 0 or C(O)-O.

The reaction according to process variant b) leads to end products of formula Ia in which X signifies 0 or C(O)-O.

As the alkylating agent (under which there are to be understood agents for the introduction of an alkyl, an alkenyl or an alkynyl group) for this process variant there is conveniently used a C$_{1-4}$-alkyl, C$_{2-4}$-alkenyl or $C_{3 \text{ or } 4}$-alkynyl halide, especially the respective chloride or bromide, or sulphate. The reaction is conveniently carried out in the presence of an inert aprotic or protic solvent such as a lower alcohol, e.g. ethanol; an aliphatic or cyclic ether, e.g. 1,2-dimethoxyethane, tetrahydrofuran or dioxan; an aliphatic ketone, e.g. acetone; acetonitrile; dimethylformamide; or dimethyl sulphoxide, or a mixture of one or more of these solvents with water, as well as in the presence of a base, such as sodium hydride, an alkali metal carbonate, especially sodium carbonate or potassium carbonate, or an alkali metal bicarbonate, especially sodium bicarbonate or potassium bicarbonate, at temperatures between 0° C. and 100° C. preferably between room temperature and 50° C. Acetone, acetonitrile and dimethylformamide are the preferred solvents. After working-up the reaction mixture the desired end product of formula Ia can be liberated from any remaining starting materials and/or byproducts according to methods known per se, e.g. column chromatography and/or crystallization.

The reaction according to process variant (c) leads to end products of formula Ia or Ib in which X signifies O, O-C(O) or O-C(O)-O. Depending on the nature of the residue $X'$-$R^1$ this process variant is an alkylation (under which there is to be understood the introduction of an alkyl, alkenyl, alkynyl, alkoxyalkyl or alkylideneaminooxyalkyl group) or acylation, which can be carried out in a manner known per se. However, additional reaction steps and/or different substitution or addition reactions on the group $X'$-$R^1$ which lead to further groups $X'$-$R^1$ are not excluded from this process variant.

As a typical example of an alkylation, a compound of formula IVa or IVb is converted into a compound of formula Ia or Ib in which X-$R^1$ signifies $C_{2-6}$-alkynoxy, e.g. propargyloxy. This is conveniently carried out by treating the compound IVa or IVb in an inert aprotic, polar solvent such as, for example, acetone, dimethylformamide, dimethyl sulphoxide or acetonitrile with a $C_{2-6}$-alkynyl halide, especially the chloride or bromide, and a base, e.g. sodium or potassium carbonate, at temperatures between room temperature and about 80° C.

As a typical example of an acylation, a compound of formula IVa or IVb is converted into a compound of formula Ia or Ib in which X-$R^1$ signifies $C_{2-9}$-alkoxycarbonyloxy, e.g. methoxycarbonyloxy. The reaction is conveniently carried out by treating the compound IVa or IVb in an inert aprotic solvent such as dimethylformamide, dimethyl sulphoxide, acetonitrile, an aliphatic ether, e.g. 1,2-dimethoxyethane, or a chlorinated, aliphatic hydrocarbon, e.g. methylene chloride, with a base such as, for example, sodium hydride, triethylamine or pyridine, and subsequently with a $C_{2-9}$-alkoxycarbonyl halide in the same solvent at temperatures between room temperature and about 80° C. The reaction is preferably carried out in methylene chloride in the presence of triethylamine or pyridine at room temperature, and methyl chloroformate is subsequently introduced, also at room temperature.

The reaction according to process variant (d) leads to end products of formula Ia or Ib in which X signifies C(O)-O. This process variant is an esterification of a substituted benzoic acid or of a reactive derivative thereof, which can also be carried out according to methods known per se. Thus, for example, a salt of the benzoic acid of formula Va or Vb is reacted with a $C_{1-8}$-alkyl, $C_{2-6}$-alkenyl, $C_{2-6}$-alkynyl or $C_{2-8}$-alkoxyalkyl chloride, bromide, iodide, sulphate, mesylate or tosylate or with the corresponding derivative of the [(alkylideneamino)oxy]methanol or -ethanol $R^6R^7C{=}N\text{-}O\text{-}(CH_2)_m\text{-}OH$ in an inert diluent at temperatures between room temperature and 100° C., e.g. at the reflux temperature of the reaction mixture, preferably in the temperature range of 40° C. to 70° C. As salts of the benzoic acid of formula Va or Vb there come into consideration especially alkali metal salts, e.g. the sodium, potassium or lithium salt, alkaline earth metal salts, e.g. the magnesium, calcium or barium salt, and salts with organic bases such as tertiary amines, e.g. triethylamine, 1,5-diaza-bicyclo[4,3,0]non-5-ene, 1,8-diaza-bicyclo[5,4,0]undec-7-ene and 1,4-diaza-bicyclo[2,2,2]octane, the alkali metal salts, especially the sodium salt and the potassium salt, being preferred. The diluents which may be used are preferably inert organic solvents such as lower alkanols, e.g. ethanol, aliphatic and cyclic ethers, e.g. diethyl ether, tetrahydrofuran and dioxan, ketones, e.g. acetone and 2-butanone, dimethylformamide, dimethyl suphoxide and hexamethylphosphoric acid triamide. The salt can be produced in situ by converting the acid with a suitable inorganic base, e.g. an alkali metal or alkaline earth metal carbonate or bicarbonate, or organic base into the salt and this can subseguently be reacted in the same reaction medium with the second reaction partner.

When an acid halide of the benzoic acid of formula Va or Vb is used as the reactive derivative, this is conveniently reacted with a $C_{1-8}$-alkanol, $C_{2-6}$-alkenol, $C_{2-6}$-alkynol, $C_{2-8}$-alkoxyalkanol or an alcohol $R^6R^7C{=}N\text{-}O\text{-}(CH_2)_m\text{-}OH$ in an inert organic solvent such as an aliphatic or cyclic ether, e.g. diethyl ether, tetrahydrofuran or dioxan, an aliphatic or aromatic hydrocarbon, e.g. n-hexane, benzene or toluene, or a halogenated, especially chlorinated, hydrocarbon, e.g. methylene chloride, chloroform or carbon tetrachloride, at temperatures of about $-20°$ C., to 100° C., preferably of 0° C. to 50° C. Moreover, the reaction is conveniently carried out in the presence of an acid-binding agent such as an organic base, e.g. triethylamine, pyridine, 1,5-diaza-bi-cyclo[4,3,0]non-5-ene, 1,8-diaza-bicyclo[5,4,0]undec- 7-ene or 1,4-diaza-bicyclo[2,2,2]octane. The acid halide is preferably the acid chloride.

As further reactive derivatives of the benzoic acid of formula Va or Vb which come into consideration there may be named the corresponding 0-acyl-1,3-dicyclohexylisourea and the corresponding N-acylimidazole or acid anhydride. Such derivatives can be reacted in the same manner as the acid halide with a $C_{1-8}$-alkanol, $C_{2-6}$-alkenol, $C_{2-6}$-alkynol, $C_{2-8}$-alkoxyalkanol or an alcohol $R^6R^7C{=}N\text{-}O\text{-}(CH_2)_m\text{-}OH$ in order to arrive at the desired benzoates. In these cases, however, the use of an acid-binding agent is unnecessary.

The starting materials of formulae IIa and IIb, which are novel, can be produced from the 3-aryluracils of formula I' given above by treating such a 3-aryluracil with a chlorinating or brominating agent. For this purpose there may be used as the halogenating agent especially phosphorus pentachloride or phosphorus oxychloride or phosphorus pentabromide or phosphoryl bromide. If desired, a mixture of phosphorus pentachloride and phosphorus oxychloride or of phosphorus pentabromide and phosphoryl bromide is used, whereby an excess of phosphorus oxychloride or phosphoryl bromide can serve as the diluent. The chlorination or bromination can be carried out in the presence of an inert diluent, especially an aprotic organic solvent such as an aliphatic or aromatic hydrocarbon, e.g. n-hexane, benzene, toluene or a xylene; a halogenated aliphatic hydrocarbon, e.g. methylene chloride, chloroform or 1,2-dichloroethane; or a halogenated aromatic hydrocarbon, e.g. chlorobenzene, as well as—especially when phosphorus oxychloride or phosphoryl bromide is used—in the presence of an organic base such as a tertiary amine, e.g. pyridine or N,N-dimethylaniline. The reaction temperatures are generally between 0° C. and the reflux temperature of the reaction mixture, preferably between 20° C. and 70° C.

In this manner thee is obtained in certain cases a mixture of the two compounds IIa and IIb. If desired, such mixtures can be separated and the individual isomers can be subjected to the reaction with the compound III or, preferably, the isomer mixture IIa/IIb can be reacted with the compound III and thereafter the end product can be separated, if desired, into the individual compounds Ia and Ib. Such separations can be carried out according to methods known per se.

The novel compounds IIa and IIb are also provided by the present invention.

The 3-aryluracils of formula I' are also novel; these can be produced in a manner known per se, for example in accordance with the following Reaction Scheme in which $R^1$-$R^5$ and X have the significances given above and $R^8$ and $R^9$ each signify lower alkyl, preferably $C_{1-4}$-alkyl:

Reaction Scheme

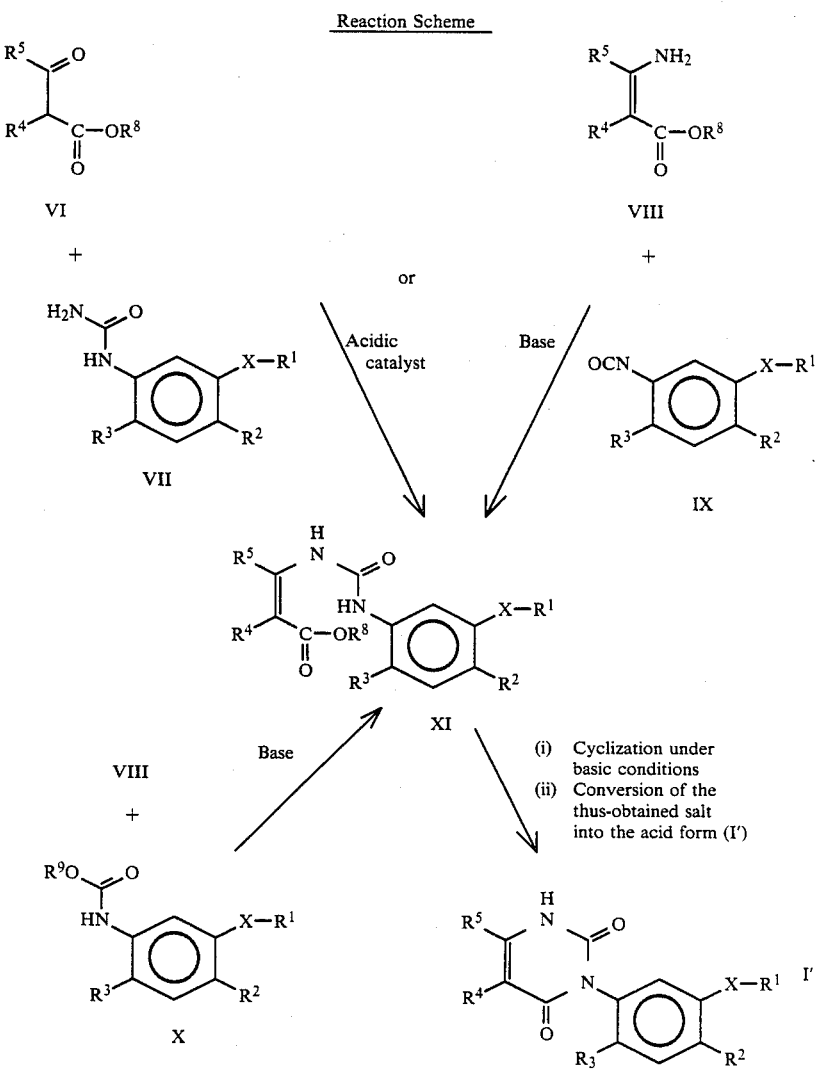

The compounds of formulae VI and VII are conveniently reacted with one another in an essentially anhydrous diluent and in the presence of an acidic catalyst at an elevated temperature. As diluents there come into consideration especially organic solvents which form azeotropes with water, such as aromatics, e.g. benzene, toluene and xylenes; halogenated hydrocarbons such as methylene chloride, chloroform, carbon tetrachloride and chlorobenzene; aliphatic and cyclic ethers such as 1,2-dimethyoxyethane, tetrahydrofuran and dioxan; and cyclohexane, and as acidic catalysts there come into consideration especially strong mineral acids such as sulphuric acid and hydrochloric acid; organic acids such as p-toluenesulphonic acid; phosphorus-containing acids such as orthophosphoric acid and polyphosphoric acid; and acidic cation exchangers such as "Amberlyst 15" (Fluka). The reaction is generally carried out in a temperature range of about 70° C to 120° C, preferably at the reflux temperature of the reaction mixture. Under these reaction conditions the desired rapid removal of the water formed in the reaction is achieved.

The reaction of the compounds of formulae VIII and IX with one another is conveniently effected in the presence of an essentially anhydrous aprotic organic solvent such as an aliphatic or cyclic ether, e.g. diethyl ether, 1,2-dimethoxyethane, tetrahydrofuran or dioxan, an aliphatic or aromatic hydrocarbon, e.g. n-hexane, benzene, toluene or a xylene, or a halogenated, aliphatic hydrocarbon, e.g. methylene chloride, chloroform, carbon tetrachloride or 1,2-dichloroethane; an aprotic, polar solvent such as dimethylformamide, hexamethylphosphoric acid triamide or dimethyl sulphoxide; or a mixture of two or more of the aforementioned solvents, as well as optionally in the presence of a base, especially an organic tertiary base such as triethylamine or pyridine, whereby the latter can serve not only as the solvent but also as the base, or of a metal hydride such as sodium or potassium hydride. The reaction temperatures are preferably in the range of about −70° C. to 50° C., the reaction being carried out particularly at temperatures between −30° C. and room temperature.

The reaction of the compounds of formulae VIII and X with one another is conveniently effected in an aprotic polar diluent such as dimethylformamide, 2-butanone, dimethyl sulphoxide or acetonitrile in the presence of a base such as an alkali metal or alkaline earth metal alcoholate or carbonate, especially a sodium alkanolate or sodium carbonate, or of a metal hydride, especially lithium or sodium hydride, at temperatures between 80° C. and 180° C., preferably at the reflux temperature of the reaction mixture. Where an alcoholate is used as the base, the alcohol which is liberated in the course of the reaction is conveniently distilled off continuously. In this method the thus-produced compound of formula XI is normally produced in situ, since the reaction conditions which are used favour the cyclization of the compound XI via the salt to the compound of formula I'.

The cyclization of the compound of formula XI, if this does not already proceed in situ, can be conveniently carried out by treating it in an inert protic organic solvent such as an alcohol, e.g. methanol, ethanol or isopropanol; an inert aprotic organic solvent such as an aliphatic or cyclic ether, e.g. 1,2-dimethoxyethane, tetrahydrofuran or dioxan; or an aromatic, e.g. benzene or toluene; an inert aprotic, Polar organic solvent, e.g. dimethylformamide or dimethyl sulphoxide, whereby such solvents can be optionally used in a two-phase mixture with a hydrocarbon, e.g. n-hexane; or water with a base at temperatures between room temperature and the reflux temperature of the reaction mixture. As bases there preferably come into consideration sodium alcoholates, alkali metal hydroxides, especially sodium hydroxide and potassium hydroxide, alkali metal carbonates, especially sodium carbonate and potassium carbonate, and sodium hydride. When the last-mentioned base is used, the solvent is preferably an aliphatic or cyclic ether, dimethylformamide or dimethyl sulphoxide.

After completion of the cyclization the product is present in the form of the corresponding metal salt depending on the nature of the base which is used, for example in the form of the corresponding alkali metal salt in the case of the above-mentioned bases. The mixture which results after the cyclization is then acidified in order to convert the salt into the compound I'. A mineral acid such as hydrochloric acid or a strong organic acid such acetic acid or p-toluenesulphonic acid is preferably used for this purpose. The product can then be isolated and, if desired, purified in a manner known per se.

The uracil derivatives of formulae IVa and IVb are also novel; these can be produced by the acid-catalyzed hydrolysis of the corresponding protected phenols of the formula

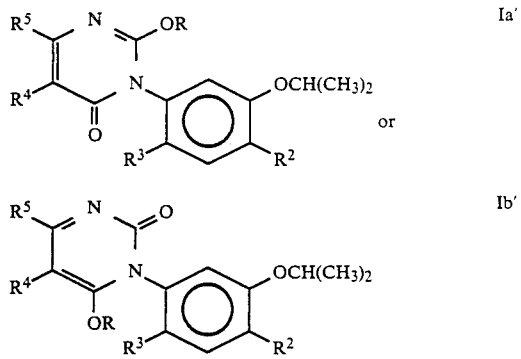

wherein R, $R^2$, $R^3$, $R^4$ and $R^5$ have the significances given above. The hydrolysis is conveniently effected in the presence of sulphuric acid as the acidic catalyst, in a chlorinated aliphatic hydrocarbon, preferably methylene chloride, as the solvent and at temperatures between −30° C. and 30° C., preferably between 0° C. and room temperature. Excess sulphuric acid can itself serve as the solvent without the need for additional solvent. The above starting materials of formulae Ia' and Ib' are a sub-group of compounds of formulae Ia and Ib, respectively. The novel compounds IVa and IVb are also provided by the present invention.

The benzoic acids of formulae Va and Vb as well as their reactive derivatives are also novel. The benzoic acids can be produced by hydrolyzing the corresponding enol ethers of formulae Ia and Ib given above in which X signifies C(O )-O. This hydrolysis can be effected according to methods known per se, especially using an inorganic acid and optionally in the presence of an organic solvent and/or of water. As the acid there comes into consideration preferably sulphuric acid and as organic solvents there come into consideration especially optionally chlorinated aliphatic hydrocarbons, e.g. methylene chloride and carbon tetrachloride. Excess sulphuric acid can itself serve as the solvent without the need for additional solvent. The reaction temperatures are generally between −30° C. and 30° C., preferably between 0° C. and room temperature. The reactive derivatives can be produced according to methods known per se starting from the benzoic acids.

The alcohols ROH, the alcoholates of formula III and the alkylating agents required in process variants (a) and (b) as well as the starting materials of formulae VI, VII, VIII, IX and X involved in the Reaction Scheme are either known or can be produced according to methods known per se.

The enol ethers in accordance with the invention possess herbicidal properties and are suitable for the control of weeds, including weed grasses, especially *Setaria faberii, Digitaria sanguina-lis. Poa annua, Chenopodium album. Amaranthus retroflexus, Abutilon theopharasti, Sinapsis alba, Datura stramonium* and *Sorghum halephense*, in diverse crop cultivations, especially in cotton, rice, maize, cereal and soya cultivations. Moreover, the compounds are not only pre-emergence, but also post-emergence herbicides.

The compounds of formulae IVa and IVb also possess herbicidal properties and can be used in a similar manner to the enol ethers in accordance with the invention for the control of weeds, especially the above-mentioned. The enol ethers in accordance with the invention (compounds of formulae Ia and Ib) and the compounds of formulae IVa and IVb are referred to hereinafter simply as the active substances (in accordance with the invention).

A concentration of 0.005–6.0 kg of active substance/ha, preferably 0.05–2.0 kg of active substance/ha, is usually sufficient to achieve the desired herbicidal effect.

The weed control composition in accordance with the invention contains an effective amount of at least one active substance in accordance with the invention as well as formulation adjuvants. The composition conveniently contains at least one of the following formulation adjuvants: solid carrier substances; solvents or dispersion media; tensides (wetting and emulsifying agents); dispersing agents (without tenside action); and stabilizers. With the use of these and other adjuvants the active substances in accordance with the invention, can be converted into the usual formulations such as dusts, powders, granulates, solutions, emulsions, suspensions, emulsifiable concentrates, pastes and the like.

The active substances in accordance with the invention are generally insoluble in water and can be formulated according to methods which are usual for water-insoluble compounds using the appropriate formulation adjuvants. The manufacture of the compositions can be carried out in a manner known per se, e.g. by mixing the particular active substance with solid carrier substances, by dissolution or suspension in suitable solvents or dispersion media, if necessary using tensides as wetting or emulsifying agents and/or dispersing agents, by diluting pre-prepared emulsifiable concentrates with solvents or dispersion media etc.

As solid carrier substances there essentially come into consideration: natural mineral substances such as chalk, dolomite, limestone, aluminas and silicic acid and salts thereof (for example siliceous earth, kaolin, bentonite, talc, attapulgite and montmorillonite); synthetic mineral substances such as highly dispersible silicic acid, aluminium oxide and silicates; organic substances such as cellulose, starch, urea and synthetic resins; and fertilizers such as phosphates and nitrates, whereby such carrier substances can be present e.g. as powders or as granulates.

As solvents or dispersion media there essentially come into consideration: aromatics such as benzene, toluene. xylenes and alkylnaphthalenes; chlorinated aromatics and chlorinated aliphatic hydrocarbons such as chlorobenzenes, chloroethylenes and methylene chloride; aliphatic hydrocarbons such as cyclohexane and paraffins, e.g. petroleum fractions; alcohols such as butanol and glycol, as well as their ethers and esters; ketones such as acetone, methyl ethyl ketone, methyl isobutyl ketone and cyclohexanone; and strongly polar solvents or dispersion media such as dimethylformamide, N-methylpyrrolidone and dimethyl sulphoxide, such solvents preferably having flash points of at least 30° C and boiling points of at least 50° C, and water. Among the solvents or dispersion media there also come into consideration so-called liquified gaseous extenders or carrier substances, these being products which are gaseous at room temperature and under normal pressure. Examples of such products are especially aerosol propellants such as halogenated hydrocarbons, e.g. dichlorodifluoromethane. If the weed control composition in accordance with the invention is present in the form of a pressurized pack, then a solvent is conveniently used in addition to the propellant.

The tensides (wetting and emulsifying agents) can be non-ionic compounds such as condensation products of fatty acids. fatty alcohols or fatty-substituted phenols with ethylene oxide; fatty acid esters and ethers of sugars or polyvalent alcohols; the products which are obtained from sugars or polyvalent alcohols by condensation with ethylene oxide; block polymers of ethylene oxide and propylene oxide; or alkyldimethylamine oxides.

The tensides can also be anionic compounds such as soaps; fatty sulphate esters, e.g. dodecyl sodium sulphate, octadecyl sodium sulphate and cetyl sodium sulphate; alkyl sulphonates, aryl sulphonates and fatty-aromatic sulphonates such as alkylbenzenesulphonates, e.g. calcium dodecylbenzenesulphonate, and butyl-naphthalenesulphonates; and more complex fatty sulphonates, e.g. the amid condensation products of oleic acid and N-methyltaurine and the sodium sulphonate of dioctyl succinate.

Finally, the tensides can be cationic compounds such as alkyldimethylbenzylammonium chlorides, dialkyldimethylammonium chlorides, alkyltrimethylammonium chlorides and ethoxylated quaternary ammonium chlorides.

As dispersing agents (without tenside action) there essentially come into consideration; lignin, sodium and ammonium salts of lignin sulphonic acids, sodium salts of maleic anhydride-diisobutylene copolymers, sodium and ammonium salts of sulphonated polycondensation products of naphthalene and formaldehyde, and sulphite lyes.

As dispersing agents, which are especially suitable as thickening or anti-settling agents, there can be used e.g. methylcellulose, carboxymethylcellulose, hydroxyethylcellulose, polyvinyl alcohol, alginates, caseinates and blood albumin.

Examples of suitable stabilizers are acid-binding agents, e.g. epichlorohydrin, phenyl glycidyl ether and soya epoxides; antioxidants, e.g. gallic acid esters and butylhydroxytoluene; UV-absorbers, e.g. substituted benzophenones, diphenylacrylonitrile acid esters and cinnamic acid esters; and deactivators, e.g. salts of ethylenediaminotetraacetic acid and polyglycols.

The weed control compositions in accordance with the invention can contain, in addition to the active substances in accordance with the invention, synergists and other active substances, e.g. insecticides, acaricides, fungicides, plant growth regulators and fertilizers. Such combination compositions are suitable for increasing the activity or for broadening the spectrum of activity.

The weed control compositions in accordance with the invention generally contain between 0.01 and 95 weight percent, preferably between 0.5 and 75 weight percent, of one or more active substances in accordance with the invention. They can be present e.g. in a form which is suitable for storage and transport. In such formulations, e.g. emulsifiable concentrates, the active substance concentration is normally in the higher range, preferably between 1 and 50 weight percent, especially between 10 and 20 weight percent. These formulations can then be diluted, e.g. with the same or different inert substances, to give active substance concentrations which are suitable for practical use, i.e. preferably about 0.01 to 10 weight percent, especially about 0.5 to 5 weight percent. The active substance concentrations can, however, also be smaller or greater.

As mentioned above, the manufacture of the weed control compositions in accordance with the invention can be carried out in a manner known per se.

For the manufacture of pulverous preparations the active substance in accordance with the invention, can be mixed with a solid carrier substance, e.g. by grinding together; or the solid carrier substance can be impregnated with a solution or suspension of the active substance and then the solvent or dispersion medium can be removed by evaporation, heating or sucking-off under reduced pressure. By adding tensides or dispersing agents such pulverous preparations can be made readily wettable with water, so that they can be converted into aqueous suspensions which are suitable e.g. as spray compositions.

The active substance in accordance with the invention can also be mixed with a tenside and a solid carrier substance to form a wettable powder which is dispersible in water, or it can be mixed with a solid pregranulated carrier substance to form a product in the form of a granulate.

When desired, the active substance in accordance with the invention can be dissolved in a water-immiscible solvent such as, for example, a high-boiling hydrocarbon, which conveniently contains dissolved emulsifying agent, so that the solution becomes self-emulsifying upon addition to water. Alternatively, the active substance can be mixed with an emulsifying agent and the mixture can then be diluted with water to the desired concentration. Moreover, the active substance can be dissolved in a solvent and thereafter the solution can be mixed with an emulsifying agent. Such a mixture can likewise be diluted with water to the desired concentration. In this manner there are obtained emulsifiable concentrates or ready-for-use emulsions.

The use of the weed control compositions in accordance with the invention, which forms a further object of the present invention, can be carried out according to usual application methods such as sprinkling, spraying, dusting, watering or scattering. The method in accordance with the invention for the control of weeds comprises treating the locus to be protected against weeds and/or the weeds with an effective amount of an active substance in accordance with the invention or of a weed control composition in accordance with the invention.

The following Example illustrate the invention in more detail.

I. Manufacture of the enol ethers in accordance with the invention

Example 1

1.3 ml of dimethylaniline are added to a solution of 3.35 g of isopropyl 2-chloro-5-[3,6-dihydro-2,6-dioxo-4-pentafluoroethyl -1(2H)-pyrimidinyl]-4-fluorobenzoate and 10 ml of phosphorus oxychloride while stirring at 25° C. and the reaction mixture is stirred at 75° C. for 5 hours. A further 1.3 g of dimethylaniline are subsequently added, and the mixture is stirred at 75° C. for 5 hours and thereafter heated at the reflux temperature for 1 hour. The mixture is then evaporated to dryness under reduced pressure at 70° C., the residue is dissolved in 100 ml of diethyl ether and the solution is extracted three times with 50 ml of ice-water each time. The organic phase is dried over anhydrous sodium sulphate and evaporated to dryness under reduced pressure.

The residue, a mixture of isopropyl 2-chloro-5-[2-chloro-6-oxo-4-pentafluoroethyl -1(6H)-pyrimidinyl]-4-fluorobenzoate and isopropyl 2-chloro-5-[6-chloro-2-oxo-4-pentafluoroethyl -1(2H)-pyrimidinyl]-4-fluorobenzoate, is dissolved in 20 ml of methanol and 3.8 ml of a 2N sodium methylate solution are added to the solution while stirring at 25° C. The temperature of the reaction mixture rises to 30° C. The mixture is subsequently stirred for 30 minutes and evaporated to dryness under reduced pressure. The residue is separated by chromatography on a silica gel column using n-hexane/diethyl ether (3:1). The first fraction, which still contains some diethylaniline, is dissolved in diethyl ether and the solution is extracted with 2N hydrochloric acid, washed to neutrality with water and dried over anhydrous sodium sulphate. The organic phase is evaporated to dryness under reduced pressure and the residue is recrystallized from n-hexane. There is obtained isopropyl 2-chloro-4-fluoro-5-[2-methoxy-6-oxo-4-pentafluoroethyl-1(6H)-pyrimidinyl]-benzoate, m.p. 82°–84° C. By further elution of the column with n-hexane/diethyl ether (1:2) there is obtained a second fraction which is recrystallized from diethyl ether/n-hexane. In this manner there is also obtained isopropyl 2-chloro-4-fluoro-5-[6-methoxy-2-oxo-4-pentafluoroethyl -1(2H)-pyrimidinyl]-benzoate, m.p. 127°–129° C.

Example 2 2.0 g of isopropyl 2-chloro-5-[2-chloro-6-oxo-4-trifluoromethyl-1(6H)-pyrimidinyl]-4-fluorobenzoate are added to a solution of 0.21 g of a 55% sodium hydride dispersion in 20 ml of isopropanol while stirring and cooling at 0° C. The reaction mixture is stirred at room temperature for reduced 10 minutes and evaporated to dryness under pressure. The residue is dissolved in 50 ml of diethyl ether and the solution is washed twice with 25 ml of water each time. The organic phase is dried over anhydrous sodium sulphate and evaporated to dryness, and the residue is purified by chromatography on a silica gel column using n-hexane/diethyl ether (3:1) as the eluent. There is obtained isopropyl 2-chloro-4-fluoro-5-[2-isopropoxy-6-oxo-4-trifluoromethyl-1(6H)-pyrimidinyl]-benzoate, $^1$H-NMR (CDCl$_3$, 400 MHz): 7.81 ppm (d,1H), 7.38 ppm (d,1H), 6.58 ppm (s,1H), 5.40 ppm (m,1H), 5.26 ppm (m,1H), 1.38 ppm (d,3H), 1.37 ppm (d,3H), 1.29 ppm (d,3H), 1.28 ppm (d,3H).

In an analogous manner, using isopropyl 2-chloro-5-[2-chloro-6-oxo-4-trifluoromethyl-1(6H)-pyrimidinyl]-4-fluorobenzoate and ethanol there is obtained isopropyl 5-[2-ethoxy-6-oxo-4-trfluoromethyl-1(6H)-pyrimidinyl]-2-chloro-4-fluorobenzoate, m.p. 115°–117° C.;

using isopropyl 2-chloro-5-[2-chloro-6-oxo-4-trifluoromethyl-1(6H)-pyrimidinyl]-4-fluorobenzoate and a solution of sodium hydride in allyl alchohol there is obtained isopropyl 5-[2-allyloxy-6-oxo-4-trifluoromethyl-1(6H)-pyrimidinyl]-2-chloro-4-fluorobenzoate, m.p. 94°–96° C.;

using isopropyl 2-chloro-5-[2-chloro-6-oxo-4-trifluoromethyl-1(6H)-pyrimidinyl]-4-fluorobenzoate and propargyl alcohol with pyridine there is obtained isopropyl 2-chloro-4-fluoro-5-[6-oxo-2-(2-propynyloxy)-4-trifluoromethyl-1(6H)-pyrimidinyl]-benzoate, m.p. 117°–119° C.;

using ethyl 2-chloro-5-[2-chloro-6-oxo-4-trifluoromethyl-1(6H)-pyrimidinyl]-4-fluorobenzoate and sodium ethylate in ethanol there is obtained ethyl 5-[2-ethoxy-6-oxo-4-trifluoromethyl-1(6H)-pyrimidinyl]-2-chloro-4-fluorobenzoate, m.p. 94°-96° C.;

using isopropyl 2-chloro-5-[2-chloro-6-oxo-4-pentafluoroethyl-1(6H)-pyrimidinyl]-4-fluorobenzoate and propargyl alcohol with pyridine there is obtained isopropyl 2-chloro-4-fluoro-5-[6-oxo-4-pentafluoroethyl-2-(2-propynyloxy)-1(6H)-pyrimidinyl]-benzoate, $^1$H-NMR (CDCl$_3$, 400 MHz): 7.85 ppm (d,1H), 7.41 ppm (d,1H), 6.71 ppm (s,1H), 5.27 ppm (m,1H), 5.00 ppm (d,2H), 2.53 ppm (t,1H), 1.39 ppm (d,3H), 1.38 ppm (d,3H);

using isopropyl 2-chloro-5-[2-chloro-6-oxo-4-pentafluoroethyl-1(6H)-pyrimidinyl]-4-fluorobenzoate and sodium ethylate in ethanol there is obtained isopropyl 5-[2-ethyl-6-oxo-4-pentafluoroethyl-1(6H)-pyrimidinyl]-2-chloro- 4-fluorobenzoate, $^1$H-NMR (CDCl$_3$, 400 MHz): 7.83 ppm (d,1H), 7.39 ppm (d,1H), 6.65 ppm (s,1H), 5.72 ppm (m,1H), 4.48 ppm (m,2H), 1.38 ppm (d,3H), 1.37 ppm (d,3H), 1.29 ppm (t,3H);

using isopropyl 2-chloro-5-[2-chloro-6-oxo-4-pentafluoroethyl-1(6H)-pyrimidinyl]-4-fluorobenzoate and sodium isopropylate in isopropanol there is obtained isopropyl 2-chloro-4-fluoro-5-[2-isopropoxy-6 -oxo-4-pentafluoroethyl-1(6H)-pyrimidinyl]-benzoate, $^1$H-NMR (CDCl$_3$, 400 MHz): 7 83 ppm (d,1H), 7.39 ppm (d,1H), 6.64 ppm (s,1H), 5.34 ppm (m,1H), 5.27 ppm (m,1H), 1.39 ppm (d,3H), 1.38 ppm (d,3H), 1.28 ppm (d,3H), 1.27 ppm (d,3H);

using isopropyl 2-chloro-5-[2-chloro-6-oxo-4-pentafluoroethyl-1(6H)-pyrmidinyl]-4-fluorobenzoate and a solution of sodium hydride in allyl alcohol there is obtained isopropyl 5-[2-allyloxy-6 -oxo-4-pentafluoroethyl-1(6H)-pyrimidinyl]-2-chloro-4-fluorobenzoate, $^1$H-NMR (CDCl$_3$, 400 MHz): 7.84 ppm (d,1H), 7.40 ppm (d,1H), 6.67 ppm (s,1H), 5.87 ppm (m,1H), 5.21–5.32 ppm (m,3H), 4.89 ppm (m,2H), 1.38 ppm (d,3H), 1.37 ppm (d,3H);

using 2-chloro-1-(4-chloro-2-fluoro-5-isopropoxyphenyl)-4-pentafluoroethyl-6(1H)-pyrimidinone and sodium ethylate in ethanol there is obtained 2-ethoxy-1-(4-chloro-2-fluoro-5-isopropoxyphenyl)-4-pentafluoroethyl-6(1H-NMR (CDCl$_3$, 400 MHz): 7.31 ppm (d,1H), 6.81 ppm (d,1H), 6.64 ppm (s,1H), 4.39–4.55 ppm (m,3H), 1.39 ppm (d,3H), 1.38 ppm (d,3H), 1.29 ppm (t,3H);

using 2-chloro-1-(4-chloro-2-fluoro-5-isopropoxyphenyl)-4-pentafluoroethyl-6(1H)-pyrimidinone and sodium isopropylate in isopropanol there is obtained 1-(4-chloro-2-fluoro-5-isopropoxyphenyl)-2-isopropoxy-4-pentafluoroethyl-6(1H)-pyrimidinone, $^1$H-NMR (CDCl$_3$, 400 MHz): 7.30 ppm (d,1H), 6.81 ppm (d,1H), 6.62 ppm (s,1H), 5.33 ppm (m,1H), 4.47 ppm (m,1H), 1.38 ppm (d,3H), 1.37 ppm (d,3H), 1.28 ppm (d,3H), 1.27 ppm (d,3H);

using methyl 2-chloro-5-[2-chloro-6-oxo-4-trifluoromethyl-1(6H)-pyrimidinyl]-4-fluorobenzoate and sodium ethylate in ethanol there is obtained methyl 5-[2-ethoxy-6-oxo-4-trifluoromethyl -1(6H)-pyrimidinyl]-2-chloro-4-fluorobenzoate, m.p. 96°-98° C.;

using 2-chloro-1-(4-chloro-2-fluoro-5-isopropoxyphenyl)-4-pentafluoroethyl-6(1H)-pyrimidinone and sodium propylate in n-propanol there is obtained 1-(4-chloro-2-fluoro-5-isopropoxyphenyl)-4 -pentafluoroethyl-2-(n-propoxy)-6(1H)-pyrimidinone, $^1$H-NMR (CDCl$_3$, 400 MHz): 7.31 ppm (d,1H), 6.82 ppm (d,1H), 6.63 ppm (s,1H), 4.46 ppm (m,1H), 4.36 ppm (m,2H), 1.66 ppm (m,2H), 1.38 ppm (d,3H), 1.37 ppm (d,3H), o.85 ppm (t,3H);

using 2-chloro-1-(4-chloro-2-fluoro-5-isopropoxyphenyl)-4-trifluoromethyl-6(1H)-pyrimidinone and sodium ethylate in ethanol there is obtained 2-ethoxy-1-(4-chloro-2-fluoro -5-isopropoxyphenyl)-4-trifluoromethyl-6(1H)-pyrimidinone, m.p. 101°-103° C.;

using isopropyl 2-chloro-5-[2-chloro-5-fluoro-6-oxo-4-trifluoromethyl-1(6H)-pyrimidinyl]-4-fluorobenzoate and sodium ethylate in ethanol there is obtained isopropyl 5-[2-ethoxy-5-fluoro-6-oxo-4-trifluoromethyl-1(6H)-pyrimidinyl]-2-chloro-4-fluorobenzoate, $^1$H-NMR (CDCl$_3$, 400 MHz): 7.83 ppm (d,1H), 7.40 ppm (d,1H), 5.27 ppm (m,1H), 4.48 ppm (m,2H), 1.39 ppm (d,3H), 1.38 ppm (d,3H), 1.29 ppm (t,3H);

using 2-chloro-1-(4-chloro-2-fluoro-5-isopropoxyphenyl)-4-trifluoromethyl-6(1H)-pyrimidinone and sodium propylate in n-propanol there is obtained 1-(4-chloro-2-fluoro-5-isopropoxyphenyl)-2-propoxy-4-trifluoromethyl-6(1H)-pyrimidinone, $^1$H-NMR (CDCl$_3$, 400 MHz): 7.31 ppm (d,1H), 6.80 ppm (d,1H), 6.59 ppm (s,1H), 4.31–4.51 ppm (m,3H), 1.67 ppm (m,2H), 1.38 ppm (d,3H), 1.37 ppm (d,3H), 0.85 ppm (t,3H);

using isopropyl 2-chloro-5-[2-chloro-5-fluoro-6-oxo-4-trifluoromethyl-1(6H)-pyrimidinyl]-4-fluorobenzoate and a solution of sodium hydride in allyl alcohol there is obtained isopropyl 5-[2-allyloxy-5-fluoro-6-oxo-4-trifluoromethyl-1(6H)-pyrimidinyl]-2-chloro-4-fluorobenzoate, $^1$H-NMR (CDCl$_3$, 400MHz): 7.84 ppm (d,1H), 7.41 ppm (d,1H), 5.87 ppm (m,1H), 5.24-5.32 ppm (m,3H), 4.89 ppm (m,2H), 1.38 ppm (d,3H), 1.39 ppm (d,3H);

using isopropyl 2-chloro-5-[2-chloro-5-fluoro-6-oxo-4-trifluoromethyl-1(6H)-pyrimidinyl]-4-fluorobenzoate and propargy alcohol with pyridine there is obtained isopropyl 2-chloro-4-fluoro-5-[5-fluoro-6-oxo-2-(2-propynyloxy)-4-trifluoromethyl-1(6H)-pyrimidinyl]-benzoate, $^1$H-NMR (CDCl$_3$, 400 MHz): 7.85 ppm (d,1H), 7.43 ppm (d,1H), 5.27 ppm (m,1H), 5.01 ppm (d,2H), 2.54 ppm (t,1H), 1.39 ppm (d,3H), 1.38 ppm (d,3H);

using 1-(4-bromo-2-fluoro-5-isopropoxyphenyl)-2-chloro-4-trifluoromethyl-6(1H)-pyrimidinone and sodium methylate in methanol there is obtained 1-(4-bromo-2-fluoro-5-isopropoxyphenyl)-2-methoxy-4-trifluoromethyl-6(1H)-pyrimidinone, m.p. 137° C.;

using 1-(4-bromo-2-fluoro-5-isopropoxyphenyl)-2-chloro-4-trifluoromethyl-6(1H)-pyrimidinone and sodium ethylate in ethanol there is obtained 2-ethoxy-1-(4-bromo-2-fluoro-5 -isopropoxyphenyl)-4-trifluoromethyl-6(1H)-pyrimidinone, m.p. 106°-108° C.;

using isopropyl 2-chloro-5-[2-chloro-5-fluoro-6 -oxo-4-pentafluoroethyl-1(6H)-pyrimidinyl]-4-fluorobenzoate and pyridine in ethanol there is obtained isopropyl 5-[2-ethoxy-5-fluoro-6-oxo-4-pentafluoroethyl-1(6H)-pyrimidinyl[pyrimidinyl]-2-chloro-4-fluorobenzoate, $^1$H-NMR (CDCl$_3$, 400MHz): 7.84 ppm (d,1H), 7.41 ppm (d,1H), 5.27 ppm (m,1H), 4.46 ppm (m,2H), 1.38 ppm (d,3H), 1.37 ppm (d,3H), 1.29 ppm (t,3H):

using isopropyl 2-chloro-5-[2-chloro-5-fluoro-6 -oxo-4-pentafluoroethyl-1(6H)-pyrimidinyl]-4-fluorobenzoate and pyridine in propargyl alcohol there is obtained isopropyl 2-chloro-5-[5-fluoro-6-oxo-4 -pentafluoroethyl-2-(2-propynyloxy)-1(6H)-pyrimidinyl]-4-fluorobenzoate, $^1$H-NMR (CDCl$_3$, 400 MHz): 7.86 ppm (d,1H), 7.43 ppm (d,1H), 5.27 ppm (m,1H), 4.97 ppm (d,2H), 2.53 ppm (t,1H), 1.39 ppm (d,3H), 1.38 ppm (d,3H);

using 2-chloro-1-(4-chloro-2-fluoro-5 -isopropoxyphenyl)-5-fluoro-4-trifluoromethyl-6(1H)-pyrimidinone and sodium methylate in methanol there is obtained 1-(4-chloro-2-fluoro-5-isopropoxyphenyl)-5 -fluoro-2-methoxy-4-trifluoromethyl-6(1H)-pyrimidinone, m.p. 144°-146° C.;

using isopropyl 2-chloro-5-[2-chloro-5-fluoro-6-oxo-4-trifluoromethyl-1(6H)-pyrimidinyl]-4-fluorobenzoate and sodium isopropylate in isopropanol there is obtained isopropyl 2-chloro-5-[5-fluoro-2-isopropoxy-6-oxo-4-trifluoromethyl-1(6H)-pyrimidinyl]-4-fluorobenzoate, $^1$H-NMR (CDCl$_3$, 400 MHz): 7.83 ppm (d,1H), 7.40 ppm (d,1H), 5.36 ppm (m,1H), 5.27 ppm (m,1H), 1.39 ppm (d,3H), 1.38 ppm (d,3H), 1.29 ppm (d,3H), 1.28 ppm (d,3H).

EXAMPLE 3

A mixture of 9.2 g of crude isopropyl 2-chloro-5-[3,6-dihydro-2,6-dioxo-5-fluoro-4-pentafluoroethyl -1(2H) -pyrimidinyl]-4-fluorobenzoate, 3.36 g of sodium bicarbonate and 3.78 g of dimethyl sulphate in 50 ml of anhydrous acetone is heated to reflux temperature for 3 hours. After cooling the solid constituents are filtered off under suction and the filtrate is evaporated to dryness under reduced pressure. The residue is separated by chromatography on a silica gel column using n-hexane/diethyl ether (2:1). There is obtained isopropyl 2-chloro-4-fluoro-5-[5-fluoro-2-methoxy-6-oxo-4-pentafluoroethyl -1(6H)-pyrimidinyl]-benzoate, m.p. 75°-77° C.

In an analogous manner, using 3-(4-chloro-3-isopropoxyphenyl)-6-trifluoromethyl-2,4(1H,3H)-pyrimidinedione with dimethyl sulphate and sodium bicarbonate in acetone there is obtained 1-(4-chloro-3-isopropoxyphenyl)-2-methoxy-4-trifluoromethyl -6(1H)-pyrimidinone. m.p. 55°-58° C.

EXAMPLE 4

9.51 g of isopropyl 2-chloro-5-[3,6-dihydro-2,6-dioxo-4-pentafluoroethyl -1(2H)-pyrimidinyl ]-4-fluorobenzoate are added at room temperature while stirring to a suspension of 0.93 g of a 55% sodium hydride dispersion in 25 ml of dimethylformamide and the mixture is stirred at room temperature for 30 minutes. The mixture is subsequently treated with 4.04 g of dimethyl sulphate and stirred at 50° C. for 4 hours. The reaction mixture is cooled and poured into 500 ml of water, and the aqueous solution is extracted twice with 100 ml of ethyl acetate each time. The organic phase is washed twice with 100 ml of water each time, dried over anhydrous sodium sulphate and evaporated to dryness under reduced pressure. The residue is separated by chromotography on a silica el column using n-hexane/diethyl ether (2:1) as the eluent. The product is recrystallized from n-hexane. There is obtained isopropyl 2-chloro-4-fluoro-5-[2-methoxy-6-oxo-4-pentafluoroethyl -1(6H)-pyrimidinyl]-benzoate, m.p. 82°-84° C.

In an analogous manner.

using 3-(4-chloro-2-fluoro-5-isopropoxyphenyl)-6-trifluoromethyl-2,4(1H,3H)-pyrimidinedione there is obtained 1-(4-chloro-2-fluoro-5-isopropoxyphenyl)-2-methoxy-4-trifluoromethyl-6(1H)-pyrimidinone, m.p. 117°-119° C.;

using 3-(4-chloro-2-fluoro-5-isopropoxyphenyl)-6-pentafluoroethyl-2,4(1H,3H)-pyrimidinedione with sodium bicarbonate and dimethyl sulphate in acetone there is obtained 1-(4-chloro-2-fluoro-5-isopropoxyphenyl)-2-methoxy -4-pentafluoroethyl-6(1H)-pyrimidinone, m.p. 79°-81° C.;

using 3-(4-chloro-2-fluoro-5-isopropoxyphenyl)-5-fluoro-6-pentafluoroethyl-2,4(1H,3H)-pyrimidinedione with sodium bicarbonate and dimethyl sulphate in acetone there is obtained 1-(4-chloro-2-fluoro-5-isopropoxyphenyl)-5-fluoro-2-methoxy-4-pentafluoroethyl-6(1H) -pyrimidinone, m.p. 69°-71° C.;

using isopropyl 2-chloro-5-[3,6-dihydro-2,6-dioxo-4-trifluoromethyl-1(2H)-pyrimidinyl]-4-fluorobenzoate there is obtained isopropyl 2-chloro-4-fluoro-5-[2-methoxy-6-oxo-4-trifluoromethyl-1(6H)-pyrimidinyl]-benzoate. m.p. 121°-123° C.;

using isopropyl 2-chloro-5-[3,6-dihydro-2,6-dioxo-5-fluoro-4-trifluoromethyl-1(2H)-pyrimidinyl]-4-fluorobenzoate there is obtained isopropyl 2-chloro-4-fluoro-5-[5-fluoro-2-methoxy-6-oxo-4-trifluoromethyl-1(6H) -pyrimidinyl]-benzoate, m.p. 104°-106° C.;

using ethyl 2-chloro-5-(1,2,4,5,6,7-hexahydro-2,4-dioxo-3H-cyclopenta[d]pyrimidin-3-yl)-benzoate with sodium hydride and isopropyl bromide in hexamethylphosphoric acid triamide there is obtained ethyl 2-chloro-5-(4,5,6,7-tetrahydro-2-isopropoxy-4-oxo-3H -cyclopenta[d]pyrimidin-3-yl)-benzoate. $^1$H-NMR (CDCl$_3$, 400 MHz): 7.69 ppm (d,1H), 7.54 ppm (d,1H), 7.23 ppm (q,1H), 5.30 ppm (m,1H), 4.38 ppm (q,2H), 2.79 ppm (m,4H). 2.09 ppm (m,2H), 1.38 ppm (t,3H), 1.22 ppm (d,6H).

EXAMPLE 5

A mixture of 2.0 g of 1-(4-chloro-2-fluoro-5-hydroxyphenyl)-2-methoxy-4-trifluoro methyl-6(1H)-pyrimidinone, 1.06 g of propargyl bromide and 1.64 g of potassium carbonate in 5.0 ml of anhydrous acetone is heated at boiling point for 2.5 hours while stirring. The insoluble constituents are subsequently filtered off under suction and the filtrate is evaporated to dryness under reduced pressure. The residue is dissolved in 100 ml of ethyl acetate and the solution is extracted three times with 50 ml of water each time. The organic phase is then dried over anhydrous sodium sulphate and evaporated to dryness. The residue is recrystallized from diethyl ether/n-hexane. There is obtained 1-(4-chloro-2-fluoro-5-propargyloxyphenyl)-2-methoxy-4-trifluoromethyl-6(1H)-pyrimidinone, m.p. 108°-110° C.

In an analogous manner, using 1-(4-chloro-2-fluoro-5-hydroxyphenyl)-2-methoxy-4-trifluoromethyl-6(1H)-pyrimidinone and methyl chloroformate with pyridine in methylene chloride there is obtained {2-chloro-4-fluoro-5-[2-methoxy -6-oxo-4-trifluoromethyl-1(6H)-pyrimidinyl]-phenyl} methyl 1 MHz): 7.40 ppm (d,1H), carbonate. $^1$H-NMR (CDCl$_3$, 400 MHz): 7.40 ppm (d,1H), 7.24 ppm (d,1H), 6.61 ppm (s,1H). 4.02 ppm (s,3H), 3.95 ppm (s,3H);

using 1-(4-chloro-2-fluoro-5-hydroxyphenyl)-2-methoxy-4-trifluoromethyl-6(1H)-pyrimidinone and acetyl chloride with pyridine in methylene chloride there is obtained 2-chloro-4-fluoro-5-[2-methoxy -6-oxo-4-trifluoromethyl-1(6H)-pyrimidinyl]-phenyl acetate, m.p. 110°-112° C.;

using 1-(4-chloro-2-fluoro-5-hydroxyphenyl)-2-methoxy-4-trifluoromethyl-6(1H)-pyrimidinone and methyl iodide with sodium hydride in dimethylformamide there is obtained 1-(4-chloro-2-fluoro-5-methoxyphenyl)-2-methoxy-4-trifluoromethyl-1(6H)-pyrimidinone. m.p. 167°-169° C.;

using 1-(4-chloro-2-fluoro-5-hydroxyphenyl)-2-methoxy-4-trifluoromethyl-6(1H)-pyrimidinone and chlorodimethyl ether with sodium carbonate in acetone there is obtained 1-[4-chloro-2-fluoro-5-(methoxymethoxy) -phenyl]-2-methoxy-4-trifluoromethyl-6(1H)-pyrimidinone, m.p. 97°–98° C.;

using 1-(4-chloro-2-fluoro-5-hydroxyphenyl)-2-methoxy-4-trifluoromethyl-6(1H)-pyrimidinone and allyl bromide with sodium carbonate in acetone there is obtained 1-(5-allyloxy-4-chloro-2-fluorophenyl)-2-methoxy-4-trifluoromethyl-6(1H)-pyrimidinone, m.p. 103°–104° C.;

using 1-(4-chloro-2-fluoro-5-hydroxyphenyl)-2-methoxy-4-pentafluoroethyl-6(1H)-pyrimidinone and methoxyacetyl chloride with pyridine in methylene chloride there is obtained {2-chloro-4-fluoro-5-[2-methoxy-6-oxo-4-pentafluoroethyl-1(6H)-pyrimidinyl]-phenyl}methoxyacetate, m.p. 130°–132° C.;

using 1-(4-chloro-2-fluoro-5-hydroxyphenyl)-2-methoxy-4-pentafluoroethyl-6(1H)-pyrimidinone and dimethyl sulphate with sodium carbonate in acetone there is obtained 1-(4-chloro-2-fluoro-5-methoxyphenyl)-2-methoxy-4-pentafluoroethyl-6(1H)-pyrimidinone. m.p. 123°–125° C.;

using 1-(4-chloro-2-fluoro-5-hydroxyphenyl)-2-methoxy-4-pentafluoroethyl-6(1H)-pyrimidinone and allyl bromide with sodium carbonate in acetone there is obtained 1-(5-allyloxy-4-chloro-2-fluorophenyl)-2-methoxy-4-pentafluoroethyl-6(1H)-pyrimidinone, m.p. 82°–83° C.;

using 1-(4-chloro-2-fluoro-5-hydroxyphenyl)-2-methoxy-4-pentafluoroethyl-6(1H)-pyrimidinone and propargyl chloroformate with pyridine in methylene chloride there is obtained {2-chloro-4-fluoro-5-[2-methoxy-6 -oxo-4-pentafluoroethyl-1(6H)-pyrimidinyl]-phenyl}2-propynyl carbonate, $^1$H–NMR (CDCl$_3$, 400 MHz): 7.41 ppm (d,1H), 7.28 ppm (d,1H), 6.66 ppm (s,1H), 4.88 ppm (d,2H), 4.00 ppm (s,3H), 2.61 ppm (t,1H);

using 1-(4-chloro-2-fluoro-5-hydroxyphenyl)-2-ethoxy-4-pentafluoroethyl-6(1H)-pyrimidinone and dimethyl sulphate with sodium carbonate in acetone there is obtained 2-ethoxy-1-(4-chloro-2-fluoro-5 -methoxyphenyl)-4-pentafluoroethyl-6(1H)-pyrimidinone, $^1$H–NMR (CDCl$_3$, 400 MHz): 7.33 ppm (d,1H), 6.79 ppm (d,1H), 6.65 ppm (s,1H), 4.48 ppm (m,2H), 3.89 ppm (s,3H), 1.29 ppm (t,3H);

using 1-(4-chloro-2-fluoro-5-hydroxyphenyl)-2-methoxy-4-pentafluoroethyl-6(1H)-pyrimidinone and propargyl bromide with sodium carbonate in acetone there is obtained 1-[4-chloro-2-fluoro-5-(2-propynyloxy) -phenyl]-2-methoxy-4-pentafluoroethyl-6(1H)-pyrimidinone, $^1$H–NMR (CDCl$_3$, 400 MHz): 7.35 ppm (d,1H), 6.98 ppm (d,1H), 6.67 ppm (s,1H), 4.77 ppm (m,2H), 3.99 ppm (s,3H), 2.58 ppm (t,1H);

using 2-ethoxy-1-(4-chloro-2-fluoro-5 -hydroxyphenyl)-4-trifluoromethyl-6(1H)-pyrimidinone and n-butyl chloroformate with pyridine in diethyl ether there is obtained n-butyl {5-[2-ethoxy-6-oxo-4 -trifluoromethyl-1(6H) -pyrimidinyl]-2-chloro-4-fluorophenyl} carbonate, m.p. 100°–102° C.;

using 2-ethoxy-1-(4-chloro-2-fluoro-5 -hydroxyphenyl) -4-trifluoromethyl-6(1H)-pyrimidinone and dimethyl sulphate with sodium carbonate in acetone there is obtained 2-ethoxy-1-(4-chloro-2-fluoro-5 -methoxyphenyl) -4-trifluoromethyl-6(1H)-pyrimidinone. m.p. 117°–119° C.;

using 2-ethoxy-1-(4-chloro-2-fluoro-5 -hydroxyphenyl) -4-trifluoromethyl-6(1H)-pyrimidinone and propargyl bromide with sodium carbonate in acetone there is obtained 2-ethoxy-1-[4-chloro-2-fluoro-5 -(2-propynyloxy)-phenyl]-4-trifluoromethyl-6(1H)-pyrimidinone, $^1$H–NMR (CDCl$_3$, 400 MHz): 7.34 ppm (d,1H), 6.97 ppm (d,1H), 6.60 ppm (s,1H), 4.76 ppm (m,2H), 4.50 ppm (m,2H), 2.57 ppm (t,1H), 1.29 ppm (t,3H);

using 1-(4-chloro-2-fluoro-5-hydroxyphenyl)-4-pentafluoroethyl-2-(n-propoxy)-6(1H)-pyrimidinone and propargyl bromide with sodium carbonate in acetone there is obtained 1-[4-chloro-2-fluoro-5-(2-propynyloxy)-phenyl]-4-pentafluoroethyl-2-(n-propoxy)-6(1H)-pyrimidinone, $^1$H–NMR (CDCl$_3$, 400 MHz): 7.34 ppm (d,1H), 6.98 ppm (d,1H), 6.65 ppm (s,1H), 4.76 ppm (m,2H), 4.36 ppm (m,2H), 2.56 ppm (t,1H), 1.67 ppm (m,2H), 0.85 ppm (t,3H);

using 2-ethoxy-1-(4-chloro-2-fluoro-5 -hydroxyphenyl) -4-pentafluoroethyl-6(1H)-pyrimidinone and propargyl bromide with sodium carbonate in acetone there is obtained 2-ethoxy-1-[4-chloro-2-fluoro-5 -(2-propynyloxy)-phenyl]-4-pentafluoroethyl-6(1H)-pyrimidinone, $^1$H–NMR (CDCl$_3$, 400 MHz): 7.35 ppm (d,1H), 6.98 ppm (d,1H), 6.65 ppm (s,1H), 4.77 ppm (m,2H), 4.48 ppm (m,2H), 2.57 ppm (t,1H), 1.29 ppm (t,3H);

using 2-ethoxy-1-(4-chloro-2-fluoro-5-hydroxyphenyl)-4-trifluoromethyl-6(1H)-pyrimidinone and isobutyryl chloride with pyridine in diethyl ether there is obtained {5-[2-ethoxy-6-oxo-4-trifluoromethyl-1(6H)-pyrimidinyl]-2-chloro-4-fluorophenyl} isobutyrate, $^1$NMR (CDCl$_3$, 400 MHz): 7.38 ppm (d,1H), 7.13 ppm (d,1H), 6.58 ppm (s,1H), 4.50 ppm (m,2H), 2.87 ppm (m,1H), 1.35 ppm (d,3H), 1.34 ppm (d,3H), 1.31 ppm (t,3H);

using 2-ethoxy-1-(4-chloro-2-fluoro-5-hydroxyphenyl)-4-pentafluoroethyl-6(1H)-pyrimidinone and 2-methoxyethyl chloroformate with pyridine in diethyl ether there is obtained {5-[2-ethoxy-6-oxo-4-pentafluoroethyl-1(6H) -pyrimidinyl]-2-chloro-4-fluorophenyl} 2-methoxyethyl carbonate, $^1$H–NMR (CDCl$_3$, 400 MHz): 7.39 ppm (d,1H), 7.26 ppm (d,1H), 6.64 ppm (s,1H), 4.39°–4.56 ppm (m,4H), 3.70 ppm (m,2H), 3.43 ppm (s,3H), 1.30 ppm (t,3H):

using 1-(4-bromo-2-fluoro-5-hydroxyphenyl)-2-methoxy-4-trifluoromethyl-6(1H)-pyrimidinone and methyl iodide with sodium hydride in dimethylformamide there is obtained 1-(4-bromo-2-fluoro-5-methoxyphenyl)-2-methoxy-4-trifluoromethyl-6(1H)-pyrimidinone, m.p. 175°–177° C.;

using 1-(4-bromo-2-fluoro-5-hydroxyphenyl)-2-methoxy-4-trifluoromethyl-6(1H)-pyrimidinone and allyl bromide with sodium hydride in dimethylformamide there is obtained 1-(5-allyloxy-4-bromo-2-fluorophenyl)-2-methoxy-4-trifluoromethyl-6(1H)-pyrimidinone. m.p. 107°–110° C.;

using 1-(4-bromo-2-fluoro-5-hydroxyphenyl)-2-methoxy-4-trifluoromethyl-6(1H)-pyrimidinone and propargyl bromide with sodium hydride in dimethylformamide there is obtained 1-[4-bromo-2-fluoro-5-(2-propynyloxy)-phenyl]-2-methoxy-4-trifluoromethyl-6(1H)-pyrimidinone, m.p. 136°–138° C.

using 1-(4-chloro-2-fluoro-5-hydroxyphenyl)-5-fluoro-2-methoxy-4-trifluoromethyl-6(1H)-pyrimidinone and acryloyl chloride with sodium hydride in dimethylformamide there is obtained {2-chloro-4-fluoro-5-[5-fluoro-2-methoxy-6-oxo-4-trifluoromethyl- 1(6H)-pyrimidinyl]-phenyl} acrylate, $^1$H–NMR (CDCl$_3$, 400 MHz): 7.42 ppm d,1H), 7.21 ppm (d,1H), 6.68 ppm (q,1H), 6.35 ppm (q,1H), 6.12 ppm (q,1H), 4.00 ppm (s,3H);

using 1-(4-chloro-2-fluoro-5-hydroxyphenyl)-5-fluoro-2-methoxy-4-trifluoromethyl-6(1H)-pyrimidinone and allyl chloroformate with pyridine in diethyl ether there is obtained {2-chloro-4-fluoro-5-[5-fluoro-2-methoxy-6-oxo-4-trifluoromethyl-1(6H)-pyrimidinyl]-phenyl} 2-propenyl carbonate, $^1$H–NMR (CDCl$_3$, 400 MHz) 7.42 ppm (d,1H), 7.26 ppm (d,1H), 5.94°–6.06 ppm (m,1H), 5.45 ppm (m,1H), 5.36 ppm (m,1H), 4.78 ppm (m,2H), 4.00 ppm (s,3H);

using 1-(4-chloro-2-fluoro-5-hydroxyphenyl)-5-fluoro-2-methoxy-4-pentafluoroethyl-6(1H)-pyrimidinone and chlorodimethyl ether with sodium hydride in dimethylformamide there is obtained 1-(4-chloro-2-fluoro-5 -methoxymethoxy-phenyl)-5-fluoro-2-methoxy-4-pentafluoroethyl-6(1H)-pyrimidinone, $^1$H–NMR CDCl$_3$, 400 MHz): 7.34 ppm (d,1H), 7.13 ppm (d,1H), 5.22 ppm (q,2H), 3.98 ppm (s,3H), 3.52 ppm (s,3H);

using 1-(4-chloro-2-fluoro-5-hydroxyphenyl)-5-fluoro-2-methoxy-4-pentafluoroethyl-6(1H)-pyrimidinone and crotonoyl chloride with sodium hydride in dimethylformamide there is obtained {2-chloro-4-fluoro-5-[5-fluoro-2 -methoxy-6-oxo-4-pentafluoroethyl-1(6H) -pyrimidinyl]-phenyl} crotonate, $^1$H–NMR (CDCl$_3$, 400 MHz): 7.42 ppm (d,1H), 7.28 ppm (m,1H), 7.20 ppm (d,1H), 6.08 ppm (m,1H), 3.98 (s,3H), 2.01 ppm (q,3H);

using 1-(4-chloro-2-fluoro-5-hydroxyphenyl)-2-propoxy-4-trifluoromethyl-6(1H)-pyrimidinone and propargyl bromide with sodium carbonate in acetone there is obtained 1-[4-chloro-2-fluoro-5-(2-propynyloxy) -phenyl]-2-propoxy-4-trifluoromethyl-6(1H)-pyrimidinone, $^1$H–NMR (CDCl$_3$, 400 MHz): 7.34 ppm (d,1H), 6.98 ppm (d,1H), 6.60 ppm (s,1H), 4.76 ppm (m,2H), 4.39 ppm (m,2H), 2.56 ppm (t,1H), 1.67 ppm (m,2H), 0.85 ppm (t,3H);

using 2-ethoxy-1-(4-bromo-2-fluoro-5-hydroxyphenyl)-4-trifluoromethyl-6(1H)-pyrimidinone and propargyl bromide with sodium hydride in dimethylformamide there is obtained 2-ethoxy-4-[bromo-2-fluoro-5-(2-propynyloxy) -phenyl]-4-trifluoromethyl-6(1H)-pyrimidinone, m.p. 101°–102° C.;

using 2-ethoxy-1-(4-bromo-2-fluoro-5-hydroxyphenyl)-4-trifluoromethyl-6(1H)-pyrimidinone and allyl bromide with sodium hydride in dimethylformamide there is obtained 2-ethoxy-1-[4-bromo-2-fluoro-5-(2-propenyloxy)-phenyl]-4-trifluoromethyl-6(1H)-pyrimidinone, m.p. 68°–70° C.;

using 2-ethoxy-1-(4-bromo-2-fluoro-5-hydroxyphenyl)-4-trifluoromethyl-6(1H)-pyrimidinone and methyl iodide with sodium hydride in dimethylformamide there is obtained 2-ethoxy-1-(4-bromo-2-fluoro-5-methoxyphenyl)-4-trifluoromethyl-6(1H)-pyrimidinone, m.p. 126°–128° C.

EXAMPLE 6

A solution of 0.80 g of 2-[(isopropylideneamino)oxy]-ethanol and 0.54 g of pyridine in 25 ml of diethyl ether is added dropwise during 15 minutes while stirring at 0° C. to a solution of 2.10 g of trifluoromethanesulphonic anhydride in 50 ml of diethyl ether and the mixture is stirred at 0° C. for 15 minutes. The clear solution is pipetted off from insoluble constituents. There is obtained 2-[(isopropylideneamino)oxy]-ethyl trifluoromethanesulphonate which is used in the next step without purification.

1.70 g of 1-(4-chloro-2-fluoro-5-hydroxyphenyl)-2-methoxy-4-trifluoromethyl-6(1H)-pyrimidinone are added at room temperature while stirring to a suspension of 0.22 g of a 55% sodium hydride dispersion in 25 ml of dimethylformamide and the mixture is stirred for 1 hour. Subsequently, the previously prepared solution of 2-[(isopropylideneamino)oxy]-ethyl trifluoromethanesulphonate is added at 0° C. and the mixture is stirred for 30 minutes. The reaction mixture is washed twice with 100 ml of water each time and the organic phase is dried over anhydrous sodium sulphate and evaporated to dryness under reduced pressure. The residue is purified by chromatography on a silica gel column using n-hexane/diethyl ether (2:1) as the eluent. The product is recrystallized from n-hexane/diethyl ether. There is obtained 1-[4-chloro-2-fluoro-5-{2-[(isopropylideneamino)oxy] -ethoxy} -phenyl]-2-methoxy-4-trifluoromethyl-6(1H)-pyrimidinone, m.p. 136°–138° C.

In an analogous manner, using 2-ethoxy-1-(4-bromo-2 -fluoro-5-hydroxyphenyl)-4-trifluoromethyl-6(1H) -pyrimidinone there is obtained 2-ethoxy-1-[4-bromo-2-fluoro-5 -{2-[(isopropylideneamino)oxy]-ethoxy}-phenyl]-4 -trifluoromethyl-6(1H) -pyrimidinone, m.p. 131°–132° C.;

using 1-(4-bromo-2-fluoro-5-hydroxyphenyl)-2-methoxy-4-trifluoromethyl-6(1H)-pyrimidinone there is obtained 1-[4-bromo-2-fluoro-5-{2-[(isopropylideneamino)oxy]-ethoxy}-phenyl]-2-methoxy-4-trifluoromethyl-6(1H) -pyrimidinone, m.p. 149°–150° C.

EXAMPLE 7

0.74 g of N,N'-dicyclohexylcarbodiimide is added while stirring at room temperature to a solution of 1.60 g of 1-(4-chloro-2-fluoro-5-hydroxyphenyl)-5-fluoro-2-methoxy-4-pentafluoroethyl-6(1H)-pyrimidinone, 0.30 g of 4-pentynoic acid and 0.05 g of 4-pyrrolidino-pyridine in 50 ml of methylene chloride and the mixture is stirred at room temperature for 5 hours. Insoluble constituents are subsequently filtered off under suction and the filtrate is evaporated to dryness. The residue is purified by chromatography on a silica gel column using n-hexane/diethyl ether (3:1) as the eluent. The product is recrystallized from n-hexane/diethyl ether. There is obtained 2-chloro-4-fluoro-5-[5-fluoro-2 -methoxy-6-oxo-4-pentafluoroethyl-1(6H)-pyrimidinyl]-phenyl 4-pentynoate, m.p. 107°–109° C.

EXAMPLE 8

A suspension of 1.90 g of 2-chloro-4-fluoro-5-[2-methoxy-6 -oxo-4-trifluoromethyl-1(6H)-pyrimidinyl]-benzoic acid in 10 ml of benzene and 1.85 g of thionyl chloride is heated for 4 hours while stirring until a solution forms. The reaction mixture is evaporated to dryness under reduced pressure, the residue is dissolved in 20 ml of methylene chloride and the solution is treated at room temperature with 5 ml of n-butanol and 0.50 g of pyridine while stirring. The reaction mixture is stirred for 3 hours and evaporated to dryness under reduced pressure. The residue is dissolved in 100 ml of ethyl acetate, the solution is washed three times with 50 ml of water each time, the organic phase is dried over anhydrous sodium sulphate and evaporated to dryness. The resinous residue is purified by chromatography on silica gel using diethyl ether/n-hexane (1:3) as the eluent. There is obtained n-butyl 2-chloro-4-fluoro-5-[2- methoxy-6-oxo-4-trifluoromethyl-1(6H)-pyrimidinyl]-benzoate. ¹H-NMR (CDCl₃: 400 MHz): 7.84 ppm (d,1H), 7.40 ppm (d,1H), 6.63 ppm (s,1H), 4.34 ppm (m,2H), 4.02 ppm (s,3H), 1.75 ppm (m,2H), 1.46 ppm (m,2H), 0.97 ppm (t,3H), In an analogous manner, using 2-chloro-4-fluoro-5-[2-methoxy-6-oxo-4-trifluoromethyl-1(6H)-pyrimidinyl]-benzoic acid and thionyl chloride there is obtained the acid chloride and from this with 2-methoxyethanol there is obtained 2-methoxyethyl 2-chloro-4-fluoro-5-[2-methoxy-6-oxo-4-trifluoromethyl-(6H)-pyrimidinyl]-benzoate, m.p. 63°–65° C.;

using 2-chloro-4-fluoro-5-[2-methoxy-6-oxo-4-trifluoromethyl-1(6H)-pyrimidinyl]-benzoic acid and thionyl chloride there is obtained the acid chloride and from this with n-propanol there is obtained n-propyl 2-chloro-4-fluoro-5-[2-methoxy-6-oxo-4-trifluoromethyl-1(6H)-pyrimidinyl]-benzoate, m.p. 55°–57° C.;

using 2-chloro-4-fluoro-5-[2-methoxy-6-oxo-4-trifluoromethyl-1(6H)-pyrimidinyl]-benzoic acid and thionyl chloride there is obtained the acid chloride and from this with ethanol there is obtained ethyl 2-chloro-4-fluoro-5-[2-methoxy-6-oxo-4-trifluoromethyl-1(6H)-pyrimidinyl]-benzoate. m.p. 91°–93° C.;

using 2-chloro-4-fluoro-5-[2-methoxy-6-oxo-4-trifluoromethyl-1(6H)-pyrimidinyl]-benzoic acid and thionyl chloride there is obtained the acid chloride and from this with methanol there is obtained methyl 2-chloro-4-fluoro-5-[2-methoxy-6-oxo-4-trifluoromethyl-1(6H)-pyrimidinyl]-benzoate, m.p. 115°–117° C.:

using 2-chloro-4-fluoro-5-[5-fluoro-2-methoxy-6-oxo-4-trifluoromethyl-1(6H)-pyrimidinyl]-benzoic acid and thionyl chloride there is obtained the acid chloride and from this with ethanol there is obtained ethyl 2-chloro-4-fluoro-5-[5-fluoro-2-methoxy-6-oxo-4-trifluoromethyl-1(6H)pyrimidinyl]-benzoate. m.p. 69°–72° C.;

using 2-chloro-4-fluoro-5-[5-fluoro-2-methoxy-6-oxo-4-trifluoromethyl-1(6H)-pyrimidinyl]-benzoic acid and thionyl chloride there is obtained the acid chloride and from this with n-propanol there is obtained n-propyl 2-chloro-4-fluoro-5-[5-fluoro-2-methoxy-6-oxo-4-trifluoromethyl-1(6H)-pyrimidinyl]-benzoate, m.p. 76°–78° C.;

using 2-chloro-4-fluoro-5-[5-fluoro-2-methoxy-6-oxo-4-trifluoromethyl-1(6H)-pyrimidinyl]-benzoic acid and thionyl chloride there is obtained the acid chloride and from this with n-butanol there is obtained n-butyl 2-chloro-4-fluoro-5-[5-fluoro-2-methoxy-6-oxo-4-trifluoromethyl-1(6H)-pyrimidinyl]-benzoate, ¹H-NMR (CDCl₃, 400 MHz): 7.85 ppm (d,1H), 7.42 ppm (d,1H), 4.35 ppm (m,2H), 4.00 ppm (s,3H), 1.75 ppm (m,2H), 1.46 ppm (m,3H);

using 2-chloro-4-fluoro-5-[5-fluoro-2-methoxy-6-oxo-4-trifluoromethyl-1(6H)-pyrimidinyl]-benzoic acid and thionyl chloride there is obtained the acid chloride and from this with 2-methoxyethanol there is obtained 2-methoxyethyl 2-chloro-4-fluoro-5-[5-fluoro-2-methoxy-6-oxo-4-trifluoromethyl-1(6H)-pyrimidinyl]-benzoate, ¹H-NMR (CDCl₃, 400 MHz): 7.88 ppm (d,1H), 7.42 ppm (d,1H), 4.49 ppm (m,2H), 4.00 ppm (s,3H), 3.71 ppm (m,2H), 3.41 ppm (s,3H)

using 2-chloro-4-fluoro-5-[5-fluoro-2-methoxy-6-oxo-4-trifluoromethyl-1(6H)-pyrimidinyl]-benzoic acid and thionyl chloride there is obtained the acid chloride and from this with methanol there is obtained methyl 2-chloro-4-fluoro-5-[5-fluoro-2-methoxy-6-oxo-4-trifluoromethyl-1(6H)-pyrimidinyl]-benzoate, ¹H-NMR (CDCl₃, 400 MHz): 7.90 ppm (d,1H), 7.43 ppm (d,1H), 4.00 ppm (s,3H), 3.94 ppm (s,3H);

using 2-chloro-4-fluoro-5-[2-methoxy-6-oxo-4-pentafluoroethyl-1(6H)-pyrimidinyl]-benzoic acid and thionyl chloride there is obtained the acid chloride and from this with methanol there is obtained methyl 2-chloro-4-fluoro-5-[2-methoxy-6-oxo-4-pentafluoroethyl-1(6H)-pyrimidinyl]-benzoate. m.p. 80°–82° C.;

using 2-chloro-4-fluoro-5-[2-methoxy-6-oxo-4-pentafluoroethyl-1(6H)-pyrimidinyl]-benzoic acid and thionyl chloride there is obtained the acid chloride and from this with ethanol there is obtained ethyl 2-chloro-4-fluoro-5-[2-methoxy-6-oxo-4-pentafluoroethyl-1(6H)-pyrimidinyl]-benzoate. ¹H-NMR (CDCl₃, 400 MHz): 7.87 ppm (d,1H), 7.40 ppm (d,1H), 6.67 ppm (s,1H), 4.40 ppm (m,2H), 4.00 ppm (s,3H), 1.40 ppm (t,3H);

using 2-chloro-4-fluoro-5-[2-methoxy-6-oxo-4-pentafluoroethyl-1(6H)-pyrimidinyl]-benzoic acid and thionyl chloride there is obtained the acid chloride and from this with n-propanol there is obtained n-propyl 2-chloro-4-fluoro-5-[2-methoxy-6-oxo-4-pentafluoroethyl-1(6H)-pyrimidinyl]-benzoate, ¹H-NMR (CDCl₃, 400 MHz): 7.86 ppm (d,1H), 7.40 ppm (d,1H), 6.67 ppm (s,1H), 4.30 ppm (m,2H), 4.00 ppm (s,3H), 1.80 ppm (m,2H), 1.02 ppm (t,3H);

using 2-chloro-4-fluoro-5-[2-methoxy-6-oxo-4-pentafluoroethyl-1(6H)-pyrimidinyl]-benzoic acid and thionyl chloride there is obtained the acid chloride and from this with n-butanol there is obtained n-butyl 2-chloro-4-fluoro-5-[2-methoxy-6-oxo-4-pentafluoroethyl-1(6H)-pyrimidinyl]-benzoate, ¹H-NMR (CDCl₃, 400 MHz): 7.86 ppm (d,1H), 7.40 ppm (d,1H), 6.68 ppm (s,1H), 4.34 ppm (m,2H), 4.00 ppm (s,3H), 1.75 ppm (m,2H), 1.46 ppm (m,2H), 0.97 ppm (t,3H);

using 2-chloro-4-fluoro-5-[2-methoxy-6-oxo-4-pentafluoroethyl-1(6H)-pyrimidinyl]-benzoic acid and thionyl chloride there is obtained the acid chloride and from this with 2-methoxyethanol there is obtained 2-methoxyethyl 2-chloro-4-fluoro-5-[2-methoxy-6-oxo-4pentafluoroethyl-1(6H)-pyrimidinyl]-benzoate, m.p. 92°–94° C.;

using 2-chloro-4-fluoro-5-[2-methoxy-6-oxo-4-trifluoromethyl-1(6H)-pyrimidinyl]-benzoic acid and thionyl chloride there is obtained the acid chloride and from this with 2-[(isopropylideneamino)oxy]-ethanol there is obtained 2-[(isopropylideneamino)oxy]-ethyl 2-chloro-4-fluoro-5-[2-methoxy-6-oxo-4-trifluoromethyl-1(6H)-pyrimidinyl]-benzoate, ¹H14 NMR (CDCl₃, 400 MHz): 7.89 ppm (d,1H), 7.40 ppm (d,1H), 6.62 ppm (s,1H), 4.56 ppm (m,2H), 4.32 ppm (m,2H), 4.02 ppm (s,3H), 1.85 ppm (s,3H), 1.83 ppm (s,3H),

II. PRODUCTION OF THE STARTING MATERIALS OF FORMULA I'

EXAMPLE 9

A solution of 3.55 g of ethyl 3-amino-4,4,4-trifluorocrotonate in 50 ml of n-hexane is added dropwise while stirring at 0°–3° C. during 15 minutes to 0.85 g of a 55% sodium hydride dispersion in 50 ml of dimethylformamide and the mixture is stirred for 30 minutes. A solution of 5.0 g of isopropyl 2-chloro-4-fluoro-5-isocyanatobenzoate in 100 ml of n-hexane is subsequently added dropwise during 5 minutes while stirring and cooling at −15° C. The temperature of the reaction mixture rises to 10° C. and the mixture is thereafter stirred at room temperature for one hour. The intermediate isopropyl 2-chloro-4-fluoro-5-[3-(2-ethoxycarbonyl -1-trifluoromethyl-vinyl)ureido]-benzoate which thereby separates is not isolated.

The mixture is brought to pH 4 by the addition of concentrated acetic acid and poured into 750 ml of water and the aqueous mixture is extracted with 300 ml of ethyl acetate. The organic phase is dried over anhydrous sodium sulphate and subsequently evaporated to dryness under reduced pressure and the residue is recrystallized from diethyl ether/n-hexane. In this manner there is obtained isopropyl 2-chloro-5-[3,6-dihydro-2,6-dioxo-4-trifluoromethyl-1(2H)-pyrimidinyl]-4-fluorobenzoate, m.p. 127°–129° C.

In an analogous manner.

using ethyl 3-amino-4,4,5,5,5-pentafluoro-2 -pentenecarboxylate and isopropyl 2-chloro-4-fluoro-5-isocyanatobenzoate there is obtained, via isopropyl 2-chloro-4-fluoro-5-[3-(2-ethoxycarbonyl-1-pentafluoroethylvinyl)ureido]-benzoate, isopropyl 2-chloro-5-[3,6-dihydro-2,6-dioxo-4-pentafluoroethyl-1(2H)-pyrimidinyl]-4 m.p. 189°–191° C.

EXAMPLE 10

A solution of 1.0 g of ethyl 3-amino-4,4,4-trifluorocrotonate in 10 ml of absolute toluene is added dropwise while stirring at 0° C. during 15 minutes to a suspension of 0.24 g of a 55% sodium hydride dispersion in 20 ml of absolute dimethylformamide and the mixture is stirred at 0° C. for 15 minutes. The reaction mixture is subsequently cooled to −30° C. and treated with a solution of 1.26 g of 4-chloro-2-fluoro-5-isopropoxyphenyl isocyanate in 10 ml of absolute toluene. The temperature rises rapidly to −10° C. and the reaction mixture is thereafter stirred at room temperature for 2 hours. The reaction mixture is poured into a solution of 3 ml of 2N hydrochloric acid and 500 ml of water and the aqueous mixture is extracted twice with 100 ml of ethyl acetate each time, and the organic phases are washed twice with 50 ml of water each time, dried over anhydrous sodium sulphate and evaporated to dryness under reduced pressure. The residue is recrystalized from diethyl ether/n-hexane. There is obtained 3-(4-chloro-2-fluoro-5-isopropoxyphenyl)-6-trifluoromethyl-2,4(1H,3H)-pyrimidinedione, m.p. 195°–197° C.

In an analogous manner, using ethyl 3-amino-4,4,5,5,5-pentafluoro-2-pentenecarboxylate and 4-chloro-2-fluoro-5-isopropoxyphenyl isocyanate there is obtained 3-(4-chloro-2-fluoro-5-isopropoxyphenyl)-6-pentafluoroethyl-2,4(1H,3H)-pyrimidinedione, m.p. 141°–143° C.;

using ethyl 3-amino-2,4,4,5,5,5-hexafluoro-2-pentenecarboxylate and 4-chloro-2-fluoro-5-isopropoxyphenyl isocyanate there is obtained 3-(4-chloro-2-fluoro-5-isopropoxyphenyl)-5-fluoro -6-pentafluoroethyl-2,4(1H, 3H)-pyrimidinedione, m.p. 160°–162° C.

EXAMPLE 11

Ammonia is conducted into a solution of 7.5 g of ethyl 3-oxo-2,4,4,4-tetrafluoro-butyrate in 20 ml of toluene at 75° C. while stirring until the solution is saturated. The reaction mixture is subsequently heated at reflux temperature for 5 hours using a water separator, whereby the intermediate ethyl 3-amino-2,4,4,4-tetrafluorocrotonate is formed.

The reaction mixture is added dropwise at 0° C. while stirring during 20 minutes to a suspension of 1.62 g of a 55% sodium hydride dispersion in 80 ml of absolute dimethylformamide and the whole is then stirred at 0° C. for 15 minutes and thereafter cooled to −5° C. A solution of 9.56 g of isopropyl 2-chloro-4-fluoro-5-isocyanatobenzoate in 40 ml of n-hexane is added thereto. The temperature of the reaction mixture rises to 10° C. and the mixture is thereafter stirred at room temperature for 3 hours. The intermediate isopropyl 2-chloro-4-fluoro-5-[3-(2-ethoxycarbonyl-2-fluoro-1-trifluoromethyl-vinyl)ureido]-benzoate which thereby separates is not isolated.

The reaction mixture is poured into 1.5 l of water which contains 20 ml of 2N hydrochloric acid and the aqueous mixture is extracted twice with 200 ml of ethyl acetate each time. The organic phase is washed with water, dried over anhydrous sodium sulphate and evaporated to dryness under reduced pressure. The residue is stirred briefly at 50° C. with 100 ml of diethyl ether and a solution of 5 g of sodium bicarbonate in 300 ml of water and cooled. After separating the aqueous phase the organic phase is extracted three times with a solution of 2.5 g of sodium bicarbonate in 100 ml of water and the combined aqueous solutions are subsequently adjusted to pH 1 with 15 ml of concentrated hydrochloric acid and extracted with diethyl ether. The organic phase is then washed with water, dried over anhydrous sodium sulphate and evaporated to dryness under reduced pressure. Finally, the residue is recrystallized from diethyl ether/n-hexane.

In this manner there is obtained isopropyl 2-chloro-5-[3,6-dihydro-2,6-dioxo-5-fluoro-4-trifluoromethyl-1(2H)-pyrimidinyl]-4-fluorobenzoate, m.p. 102°–106° C.

EXAMPLE 12

A slow stream of ammonia is conducted into a solution of 8.17 g of ethyl 3-ethoxy-2,4,4,5,5,5-hexafluoro -3-hydroxypentanecarboxylate in 30 ml of toluene during 20 hours while stirring and at the same time an azeotropic mixture of water, ethanol and toluene is distilled off slowly. Ethyl 3-amino-2,4,4,5,5,5-hexafluoro-2-pentenecarboxylate forms as the intermediate.

The reaction mixture is added dropwise at 0° C. while stirring during 15 minutes to a suspension of 1.35 g of a 55% sodium hydride dispersion in 50 ml of dimethylformamide and the whole is stirred at 0° C. for 15 minutes and thereafter cooled to −30° C. A solution of 8.0 g of isopropyl 2-chloro-4-fluoro-5-isocyanatobenzoate in 30 ml of toluene is added thereto. The temperature of the reaction mixture rises to −10° C. Thereafter. the mixture is stirred at room temperature for 3 hours. The reaction mixture is poured into 1 l of water which contains 17 ml of 2N hydrochloric acid and the aqueous mixture is extracted twice with 200 ml of ethyl acetate each time. The organic phase is washed with water, dried over anhydrous sodium sulphate and evaporated to dryness under reduced pressure. The residue is stirred vigorously with 100 ml of diethyl ether and a solution of 4.0 g of sodium bicarbonate in 200 ml of water. After separating the aqueous phase the organic phase is extracted three times with a solution of 2.5 g of sodium bicarbonate in 100 ml of water, and the combined aqueous solutions are subsequently adjusted to pH 1 with 16 ml of concentrated hydrochloric acid and extracted twice with 150 ml of diethyl ether each time. The organic phase is washed with water, dried over anhydrous sodium sulphate and evaporated to dryness under reduced pressure.

In this manner there is obtained isopropyl 2-chloro-5-[3,6-dihydro-2,6-dioxo-5-fluoro-4-pentafluoroethyl- 1(2H)-pyrimidinyl]-4-fluorbenzoate which is methylated (see Example 3) without further purification.

III. PRODUCTION OF THE STARTING MATERIALS OF FORMULA XI AND FORMULA I' (FROM XI)

EXAMPLE 13

48.4 g of ethyl 2-chloro-5-ureido-benzoate and 31.2 g of ethyl cyclopentanone-2-carboxylate are heated at reflux temperature for 6 hours in 500 ml of benzene and 2 g of toluene-4-sulphonic acid monohydrate. The water formed is removed by means of a water separator. The reaction mixture is subsequently evaporated to dryness. the residue is dissolved in 700 ml of diethyl ether and the solution is filtered. The filtrate is evaporated to dryness and the residue is purified by chromatography on 1.5 kg of silica gel using diethyl ether/n-hexane (1:2) as the eluent. Ethyl 2-chloro-5-[3-(2-ethoxycarbonyl-1-cyclopenten-1-yl)-ureido]-benzoate is obtained as colourless crystals. The product is recrystallized from diethyl ether/n-hexane, m.p. 110°-112° C.

EXAMPLE 14

A solution of 118.0 g of ethyl 2-chloro-5-[3-(2-ethoxycarbonyl-1-cyclopenten-1-yl)ureido]-benzoate in 800 ml of absolute 1,2-dimethoxyethane is added dropwise while stirring at 20° C. during 10 minutes to a suspension of 7.7 g of sodium hydride in 800 ml of absolute 1,2-dimethoxyethane. The reaction mixture is subsequently stirred for 1 hour. treated with 20 ml of acetic acid and evaporated to dryness under reduced pressure. The residue is dissolved in 2 l of methylene chloride and washed twice with 1 l of water. The organic phase is dried over anhydrous sodium sulphate and evaporated until crystallization occurs. The residue is treated with 1 l of n-hexane and the crystals are filtered off under suction and rinsed with n-hexane. There is obtained ethyl 2-chloro-5-(1,2,4,5,6,7-hexahydro-2,4-dioxo-3H-cyclopenta[d]pyrimidin-3-yl)-benzoate, m.p. 178°-180° C.

IV. PRODUCTION OF THE STARTING MATERIALS/ACTIVE SUBSTANCES OF FORMULA IVa

EXAMPLE 15

3.70 ml of concentrated sulphuric acid are added dropwise during 1 minute to a solution of 3.80 g of 1-(4-chloro-2-fluoro-5-isopropoxyphenyl) -2-methoxy-4-trifluoromethyl-6(1H)-pyrimidinone (see Example 4, 2nd part) in 10 ml of methylene chloride while stirring and cooling at room temperature. The reaction mixture is stirred at room temperature for 3 hours and poured on to 15 g of ice. The organic phase is separated and the aqueous phase is extracted twice with 5 ml of methylene chloride each time and the combined organic phases are washed twice with 10 ml of water each time. The methylene chloride solution is subsequently dried over anhydrous sodium sulphate and evaporated to dryness under reduced pressure. The residue is recrystallized from diethyl ether/n-hexane. There is obtained 1-(4-chloro-2-fluoro-5-hydroxyphenyl)-2-methoxy-4-trifluoromethyl-6(1H)-pyrimidinone, m.p. 147°-149° C.

In an analogous manner,
using 1-(4-chloro-2-fluoro-5-isopropoxyphenyl)-4-pentafluoroethyl-2-propoxy-6(1H)-pyrimidinone with concentrated sulphuric acid at 0° C. during 1.5 minutes there is obtained 1-(4-chloro-2-fluoro-5-hydroxyphenyl)-4-pentafluoroethyl-2-propoxy-6(1H)-pyrimidinone, m.p. 109°-111° C.;

using 2-ethoxy-1-(4-chloro-2-fluoro-5-isopropoxyphenyl)-4-pentafluoroethyl-6(1H)-pyrimidinone with concentrated sulphuric acid at 0° C. during 1.5 minutes there is obtained 2-ethoxy-1-(4-chloro-2-fluoro-5-hydroxyphenyl)-4-pentafluoroethyl-6(1H)-pyrimidinone, m.p. 117°-120° C.;

using 1-(4-chloro-2-fluoro-5-isopropoxyphenyl)-2-methoxy-4-pentafluoroethyl-6(1H)-pyrimidinone with concentrated sulphuric acid at room temperature during 20 minutes there is obtained 1-(4-chloro-2-fluoro-5-hydroxyphenyl)-2-methoxy-4-pentafluoroethyl-6(1H)-pyrimidinone. m.p. 143°-145° C.;

using 1-(4-bromo-2-fluoro-5-isopropoxyphenyl)-2-methoxy-4-trifluoromethyl-6(1H)-pyrimidinone with concentrated sulphuric acid there is obtained 1-(4-bromo-2-fluoro-5-hydroxyphenyl)-2-methoxy-4-trifluoromethyl-6(1H)-pyrimidinone, m.p. 132°-136° C.;

using 1-(4-chloro-2-fluoro-5-isopropoxyphenyl)-2-propoxy-4-trifluoromethyl-6(1H)-pyrimidinone with concentrated sulphuric acid during 2 minutes at 0° C. there is obtained 1-(4-chloro-2-fluoro-5-hydroxyphenyl)-2-propoxy-4-trifluoromethyl-6(1H)-pyrimidinone, m.p. 122°-123° C.

using 1-(4-chloro-2-fluoro-5-isopropoxyphenyl)-5-fluoro-2-methoxy-4-trifluoromethyl-6(1H)-pyrimidinone with concentrated sulphuric acid during 2 minutes at 0° C. there is obtained 1-(4-chloro-2-fluoro-5-hydroxyphenyl)-5-fluoro-2-methoxy-4-trifluoromethyl-6(1H)-pyrimidinone, $^1H^{14}$ NMR (CDCl$_3$, 400 MHz): 7.30 ppm (d,1H), 6.87 ppm (d,1H), 4.00 ppm (s,3H);

using 1-(4-chloro-2-fluoro-5-isopropoxyphenyl)-5-fluoro-2-methoxy-4-pentafluoroethyl-6(1H)-pyrimidinone with concentrated sulphuric acid during 2 minutes at 0° C. there is obtained 1-(4-chloro-2-fluoro-5-hydroxyphenyl)-5-fluoro-2-methoxy-4-pentafluoroethyl-6(1H)-pyrimidinone, $^1H$-NMR (CDCl$_3$, 60 MHz): 7.28 ppm (d,1H), 6.83 ppm (d,1H), 5.10 ppm (s,1H), 4.00 ppm (s,3H);

using 2-ethoxy-1-(4-bromo-2-fluoro-5-isopropoxyphenyl)-4-trifluoromethyl-6(1H)-pyrimidinone with concentrated sulphuric acid during 2 minutes at 0° C. there is obtained 2-ethoxy-1-(4-bromo-2-fluoro-5-hydroxyphenyl)-4-trifluoromethyl-6(1H)-pyrimidinone, m.p. 160°-161° C.

V. PRODUCTION OF THE STARTING MATERIALS OF FORMULA IIa

EXAMPLE 16

23.3 g of pyridine are added at room temperature while stirring and cooling to a suspension of 38.8 g of isopropyl 2-chloro-5-[3,6-dihydro-2,6-dioxo-4-trifluoromethyl-1(2H)-pyrimidinyl]-4-fluorobenzoate in 45.2 g of phosphorus oxychloride and 40 ml of toluene. A solution forms rapidly. The temperature is maintained between 30° to 35° C. and, after 15 minutes, a colourless precipitate begins to separate. The reaction mixture is stirred at 30°-35° C. for 45 minutes and is then poured onto 300 g of ice. The mixture is subsequently extracted with 200 ml of ethyl acetate and the organic phase is washed three times with 50 ml of water each time, dried over anhydrous sodium sulphate and evaporated to dryness under reduced pressure. The residue is recrystallized from n-hexane. There is obtained isopropyl 2-chloro-5-[2-chloro-6-oxo-4-trifluoromethyl-1(6H)-pyrimidinyl]-4-fluorobenzoate, m.p. 72°–75° C.

In an analogous manner.

using 3-(4-chloro-2-fluoro-5-isopropoxyphenyl)-6-trifluoromethyl-2,4(1H,3H)-pyrimidinedione with phosphorus oxychloride and pyridine within 20 minutes at 30°–35° C. and thereafter for 1 hour at 70° C. there is obtained 2-chloro-1-(4-chloro-2-fluoro-5-isopropoxyphenyl)-4-trifluoromethyl-6(1H)-pyrimidinone, m.p. 101°–103° C.;

using ethyl 2-chloro-5-[3,6-dihydro-2,6-dioxo-4-trifluoromethyl-1(2H)-pyrimidinyl]-4-fluorobenzoate with phosphorus oxychloride and pyridine within 19 hours at room temperature there is obtained ethyl 2-chloro-5-[2-chloro-6-oxo-4-trifluoromethyl-1(6H)-pyrinidinyl]-4-fluorobenzoate, m.p. 88°–90° C.;

using isopropyl 2-chloro-5-[3,6-dihydro-2,6-dioxo-4-pentafluoroethyl-1(2H)-pyrimidinyl]-4-fluorobenzoate with phosphorus oxychloride and pyridine within 1 hour at room temperature there is obtained isopropyl 2-chloro-5-[2-chloro-6-oxo-4-pentafluoroethyl-1(6H)-pyrimidinyl]4-fluorobenzoate, $^1$H-NMR (CDCl$_3$, 60 MHz): 7.90 ppm (d,1H), 7.48 ppm (d,1H), 6.96 ppm (s,1H), 5.30 ppm (m,1H), 1.40 ppm (d,6H);

using 3-(4-chloro-2-fluoro-5-isopropoxyphenyl)-6-pentafluoroethyl-2,4(1H,3H)-pyrimidinone with phosphorus oxychloride and pyridine within 30 minutes at 0°–3° C. there is obtained 2-chloro-1-(4-chloro-2-fluoro-5-isopropoxyphenyl)-4-pentafluoroethyl-6(1H)-pyrimidinone, m.p. 55°–58° C;

using methyl 2-chloro-5-[3,6-dihydro-2,6-dioxo-4-trifluoromethyl-1(2H)-pyrimidinyl]-4-fluorobenzoate with phosphorus oxychloride and pyridine within 7 hours at room temperature there is obtained methyl 2-chloro-5-[2-chloro-6-oxo-4-trifluoromethyl-1(6H)-pyrimidinyl]-4-fluorobenzoate, m.p. 89°–91° C.;

using isopropyl 2-chloro-5-[3,6-dihydro-2,6-dioxo-5-fluoro-4-trifluoromethyl-1(2H) -pyrimidinyl]-4-fluorobenzoate with phosphorus oxychloride and pyridine within 1 hour at room temperature and thereafter for 1 hour at 60° C. there is obtained isopropyl 2-chloro-5-[2-chloro-5-fluoro-6-oxo-4-trifluoromethyl-1(6H)-pyrimidinyl]4-fluorobenzoate, $^1$H-NMR (CDCl$_3$, 60 MHz): 7.88 ppm (d,1H), 7.47 ppm (d,1H), 5.30 ppm (m,1H), 1.41 ppm (d,6H);

using 3-(4-bromo-2-fluoro-5-isopropoxyphenyl)-6-trifluoromethyl-2,4(1H,3H)-pyrimidinedione with phosphorus oxychloride and pyridine there is obtained 1-(4-bromo-2-fluoro-5-isopropoxyphenyl)-2-chloro-4-trifluoromethyl-6(1H)-pyrimidinone, m.p. 102° C.;

using 3-(4-chloro-2-fluoro-5-isopropoxyphenyl)-5-fluoro-6-trifluoromethyl-2,4(1H,3H)-pyrimidinedione with phosphorus oxychloride and pyridine within 15 minutes at 20°–40° C. and thereafter for 1 hour at 70° C. there is obtained 2-chloro-1-(4-chloro-2-fluoro -5-isopropoxyphenyl)-5-fluoro-4-trifluoromethyl-6(1H)-pyrimidinone, $^1$H-NMR (CDCl$_3$, 60 MHz): 7.42 ppm (d,1H), 6.84 ppm (d,1H), 4.50 ppm (m,1H), 1.44 ppm (d,6H);

using isopropyl 2-chloro-5-[3,6-dihydro-2,6-dioxo-5-fluoro-4-pentafluoroethyl-1(2H)-pyrimidinyl]-4-fluorobenzoate with phosphorus oxychloride and pyridine within 6 hours at room temperature there is obtained isopropyl 2-chloro-5-[2-chloro-5-fluoro-6-oxo-4-pentafluoroethyl-1(6H) -pyrimidinyl]-4-fluorobenzoate, $^1$H-NMR (CDCl$_3$, 400 MHz): 7.88 ppm (d,1H), 7.48 ppm (d,1H), 5.28 ppm (m,1H), 1.39 ppm (d,6H),

VI. PRODUCTION OF THE STARTING MATERIALS OF FORMULA Va

EXAMPLE 17

A solution of 5 g of isopropyl 2-chloro-4-fluoro-5-[2-methoxy-6-oxo-4-trifluoromethyl-1(6H)-pyrimidinyl]-benzoate in 20 ml of methylene chloride is treated with 25 ml of concentrated sulphuric acid while stirring and cooling at 20°–25° C. The reaction mixture is stirred at room temperature for 20 minutes and poured onto 100 g of ice. The organic phase is separated, the aqueous phase is extracted twice with 15 ml of ethyl acetate each time and the combined organic phases are washed to neutrality with water. The solution is subsequently dried over anhydrous sodium sulphate and evaporated to dryness under reduced pressure. The resinous residue is recrystallized from diethyl ether/n-hexane. There is obtained 2-chloro-4-fluoro-5-[2-methoxy-6-oxo-4-trifluoromethyl-1(6H)-pyrimidinyl[-benzoic acid, m.p. 205°–210° C.

In an analogous manner, using isopropyl 2-chloro-4-fluoro-5-[2-methoxy-6-oxo-4-pentafluoroethyl-1(6H)-pyrimidinyl]-benzoate there is obtained 2-chloro-4-fluoro-5-[2-methoxy-6-oxo-4-pentafluoroethyl-1(6H)-pyrimidinyl]-benzoic acid, m.p. 197°–199° C.;

using isopropyl 2-chloro-4-fluoro-5-[5-fluoro-2-methoxy-6-oxo-4-trifluoromethyl-1(6H)-pyrimidinyl]-benzoate there is obtained 2-chloro-4-fluoro-5-[5-fluoro-2-methoxy-6-oxo-4-trifluoromethyl-1(6H)-pyrimidinyl]-benzoic acid, m.p. 199°–201° C.

VI. FORMULATION EXAMPLES

EXAMPLE 18

An emulsifiable concentrate contains the following ingredients:

| | |
|---|---|
| Compound of formula Ia, Ib, IVa or IVb (active substance) | 50 g/l |
| N—Methylpyrrolidone (auxiliary solvent) | 200 g/l |
| Nonylphenol-(10)ethoxylate (non-ionic emulsifier) | 50 g/l |
| Calcium dodecylbenzenesulphonate (anionic emulsifer) | 25 g/l |
| Mixture of alkylbenenes (solvent) ad | 1000 ml |

The active substance and the emulsifiers are dissolved in the auxiliary solvent while stirring and the solution is made up to 1 liter with the solvent.

The resulting emulsifiable concentrate emulsifies in water to give a ready-for-use spray liquor having the desired concentration.

EXAMPLE 19

The ingredients listed hereinafter are mixed with one another for the manufacture of a 25% spray powder:

| | |
|---|---|
| Compound of formula Ia, Ib, IVa or IVb (active substance) | 25 g |
| Silicic acid, hydrated (carrier material, grinding aid) | 5 g |
| Sodium lauryl sulphate (wetting agent) | 1 g |
| Sodium lignosulphonate (dispersing agent) | 2 g |
| Kaolin (carrier material) | 67 g |
| | 100 g |

The mixture is subsequently finely ground using a pinned disc mill or comparable milling apparatus.

Upon stirring in water the resulting spray powder gives a fine suspension which is suitable as a ready-for-use spray liquor.

We claim:

1. A compound of the formula

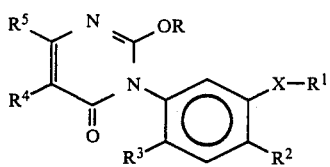

Ia or

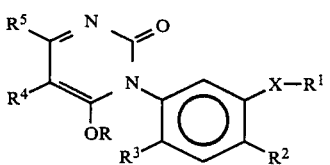

Ib wherein
R is C$_{1-4}$-alkyl, or C$_{3\,or\,4}$-alkynyl,
R$^1$ is C$_{1-8}$-alkyl, C$_{2-6}$-alkenyl, C$_{2-6}$-alkynyl, C$_{2-8}$-alkoxyalkyl or a group

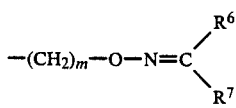

R$^2$ is halogen or cyano,
R$^3$ is halogen,
R$^4$ is hydrogen, fluorine or C$_{1-4}$-alkyl,
R$^5$ is C$_{1-4}$ alkyl or C$_{1-4}$-haloalkyl, or
R$^4$ and R$^5$ together form tri- or tetramethylene,
R$^6$ is C$_{1-4}$-alkyl,
R$^7$ is C$_{1-4}$-alkyl,
m is 1 or 2 and
X is O, O-C(O), O-C(O)-O or C(O)-O.

2. A compound according to claim 1, wherein R$^1$ is C$_{1-6}$-alkyl C$_{3-6}$-alkenyl, C$_{3-6}$-alkynyl, C$_{2-7}$-alkoxyalkyl or

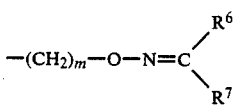

R is C$_{1-4}$-alkyl, C$_{3\,or\,4}$-alkenyl or C$_{3\,or\,4}$-alkynyl and R$^2$ is halogen.

3. A compound according claim 2, wherein R$^2$ is chlorine or bromine.

4. A compound according to claim 2, wherein R$^3$ is fluorine.

5. A compound according to claim 2, wherein R$^5$ is trifluoromethyl or pentafluoroethyl.

6. A compound according to claim 1, selected from the group consisting of
Isopropyl 2-chloro-4-fluoro-5-[2-methoxy-6-oxo-4-pentafluoroethyl-1(6H)-pyrimidinyl]-benzoate,
isopropyl 2-chloro-4-fluoro-5-[5-fluoro-2-methoxy-6-oxo-4-pentafluoroethyl-1(6H)-pyrimidinyl]-benzoate,
1-(4-chloro-2-fluoro-5-isopropoxyphenyl)-2-methoxy-4-trifluoromethyl-6(1H)-pyrimidinone,
1-(4-chloro-2-fluoro-5-isopropoxyphenyl)-2-methoxy-4-pentafluoroethyl-6(1H)-pyrimidinone,
1-(4-chloro-2-fluoro-5-isopropoxyphenyl)-5-fluro-2-methoxy-4-pentafluoroethyl-6(1H)-pyrimidinone,
isopropyl 2-chloro-4-fluoro-5-[2-methoxy-6-oxo-4-trifluoromethyl-1(6H)-pyrimidinyl]-benzoate,
isopropyl 2-chloro-4-fluoro-5-[5-fluoro-2-methoxy-6-oxo-4-trifluoromethyl-1(6H)-pyrimidinyl]-benzoate,
1-(4-chloro-2-fluoro-5-propargyloxyphenyl)-2-methoxy-4-trifluoromethyl-6(1H)-pyrimidinone,
methyl 2-chloro-4-fluoro-5-[2-methoxy-6-oxo-4-pentafluoroethyl-1(6H)-pyrimidinyl]-benzoate,
ethyl 2-chloro-4-fluoro-5-[2-methoxy-6-oxo-4-pentafluoroethyl-1-(6H)-pyrimidinyl]-benzoate,
n-propyl 2-chloro-4-fluoro-5-[2-methoxy-6-oxo-4-pentafluoroethyl-1(6H)-pyrimidinyl]-benzoate and
n-butyl 2-chloro-4-fluoro-5-[2-methoxy-6-oxo-4-pentafluoroethyl-1(6H)-pyrimidinyl]-benzoate.

7. The compound according to claim 1 which is 2-methoxyethyl 2-chloro-4-fluoro-5-[2-methoxy-6-oxo-4-pentafluoroethyl-1(6H)-pyrimidinyl]-benzoate.

8. A compound of the formula

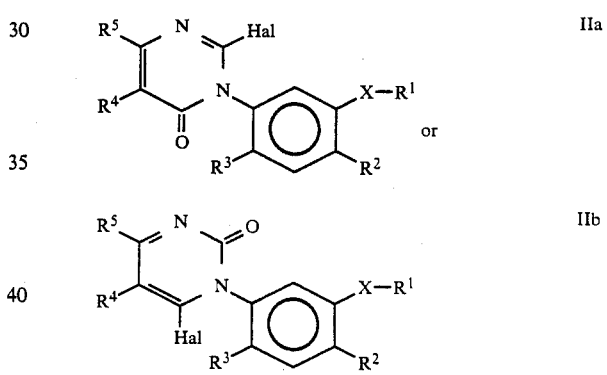

wherein
R$^1$ is C$_{1-8}$-alkyl, C$_{2-6}$-alkenyl C$_{2-6}$-alkynyl, C$_{2-8}$-alkoxyalkyl or

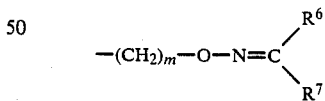

R$^2$ is halogen or cyano,
R$^3$ is halogen,
R$^4$ is hydrogen, fluorine or C$_{1-4}$-alkyl,
R$^5$ is C$_{1-4}$-alkyl or Chd 1-4-haloalkyl, or
R$^4$ and R$^5$ together form tri- or tetramethylene,
R$^6$ is C$_{1-4}$-alkyl,
R$^7$ is C$_{1-4}$-alkyl,
m is 1 or 2,
X is O, O-C(O), O-C(O)-O or C(O)-O and
Hal is chlorine or bromine.

9. A compound according to claim 8, wherein R$^1$ is C$_{1-6}$-alkyl, C$_{3-6}$-alkenyl C$_{3-6}$-alkynyl, C$_{2-7}$-alkoxyalkyl or

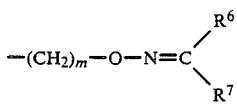

and $R^2$ is halogen.

10. A compound of the formula

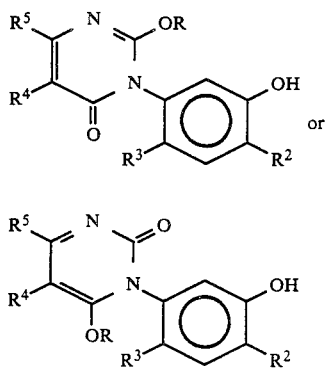

wherein

R is $C_{1-4}$-alkyl, or $C_{3 \text{ or } 4}$-alkynyl, $R^2$ is halogen or cyano, $R^3$ is halogen, $R^4$ is hydrogen, fluorine or $C_{1-4}$-alkyl and $R^5$ is $C_{1-4}$-alkyl or $C_{1-4}$-haloalkyl, or $R^4$ and $R^5$ together form tri- or tetramethylene.

11. A compound of the formula IVa according to claim 10, wherein R is $C_{1-4}$-alkyl $C_{3 \text{ or } 4}$-alkenyl or $C_{3 \text{ or } 4}$-alkynyl and $R^2$ is halogen.

12. A weed control composition which contains as an active ingredient an effective amount of a compound according to claim 1.

13. A weed control composition which contains as an active ingredient an effective amount of a compound according to claim 10.

14. A weed control composition according to claim 12 which contains as an active ingredient an effective amount of at least one compound selected from the group consisting of isopropyl 2-chloro-4-fluoro-5-[2-methoxy-6-oxo-4-pentafluoroethyl-1(6H)-pyrimidinyl]-benzoate, isopropyl 2-chloro-4-fluoro-5-[5-fluoro-2-methoxy-6-oxo-4-pentafluoroethyl-1(6H)-pyrimidinyl]-benzoate, 1-(4-chloro-2-fluoro-5-isopropoxyphenyl)-2-methoxy-4-trifluoromethyl-6(1H)-pyrimidinone, 1-(4-chloro-2-fluoro-5-isopropoxyphenyl)-2-methoxy-4-pentafluoroethyl-6(1H)-pyrimidinone, 1-(4-chloro-2-fluoro-5-isopropoxyphenyl)-5-fluoro-2-methoxy-4-pentafluoroethyl-6(1H)-pyrimidinone, isopropyl 2-chloro-4-fluoro-5-[2-methoxy-6-oxo-4-trifluoromethyl-1(6H)-pyrimidinyl]-benzoate, isopropyl 2-chloro-4-fluoro-5-[5-fluoro-2-methoxy-6-oxo-4-trifluoromethyl-1(6H)-pyrimidinyl]-benzoate, 1-(4-chloro-2-fluoro-5-propargyloxyphenyl)-2-methoxy-4-trifluoromethyl-6(1H)-pyrimidinone, methyl 2-chloro-4-fluoro-5-[2-methoxy-6-oxo-4-pentafluoroethyl-1(6H)-pyrimidinyl]-benzoate, ethyl 2-chloro-4-fluoro-5-[2-methoxy-6-oxo-4-pentafluoroethyl-1(6H)-pyrimidinyl]-benzoate.

n-propyl 2-chloro-4-fluoro-5-[2-methoxy-6-oxo-4-pentafluoroethyl-1(6H)-pyrimidinyl]-benzoate and n-butyl 2-chloro-4-fluoro-5-[2-methoxy-6-oxo-4-pentafluoroethyl-1(6H)-pyrimidinyl]-benzoate.

15. The weed control composition according to claim 12, which contains an effective amount of 2-methoxyethyl 2-chloro-4-fluoro-5-[2-methoxy-6-oxo-4-pentafluoroethyl-1(6H)-pyrimidinyl]-benzoate.

* * * * *